United States Patent

Kraehling et al.

Patent Number: 5,212,173
Date of Patent: May 18, 1993

[54] ALKYLAMINOALKYLAMINE AND ETHER COMPOUNDS, PROCESSES AND INTERMEDIATES FOR THEIR PREPARATION, AND MEDICAMENTS CONTAINING THEM

[75] Inventors: Herman Kraehling, Sehnde; Samuel David; Insa Hell, both of Hanover; Ulf Preuschoff, Laatzen; Ivan Ban, Hanover, all of Fed. Rep. of Germany; Marie-Odile Christen, Suresnes, France

[73] Assignee: Kali-Chemie Pharma GmbH, Hanover, Fed. Rep. of Germany

[21] Appl. No.: 809,448

[22] Filed: Dec. 19, 1991

[30] Foreign Application Priority Data

Dec. 19, 1990 [DE] Fed. Rep. of Germany ....... 4040633
Sep. 18, 1991 [DE] Fed. Rep. of Germany ....... 4130947

[51] Int. Cl.$^5$ ............... A61K 31/38; A61K 31/34; C07D 265/30; C07D 321/10
[52] U.S. Cl. ............... 514/237.8; 514/450; 514/452; 514/464; 514/579; 514/646; 514/649; 514/651; 514/659; 544/162; 549/350; 549/365; 549/366; 549/434; 564/1; 564/306; 564/340; 564/346; 564/440; 564/442; 564/443; 564/461; 564/462
[58] Field of Search ............... 544/162; 514/237.8, 514/649, 651, 646, 659, 579, 450, 452, 464; 564/1, 306, 340, 346, 440, 442, 443, 461, 462; 549/350, 365, 366, 434

[56] References Cited

PUBLICATIONS

Chemical Abstracts, vol. 81, No. 21, Nov. 25, 1974, Columbus, Ohio, USA, Abstract No. 130790R.
Chemical Abstracts, vol. 90, No. 11, Mar. 12, 1979, Columbus, Ohio, USA, Abstract No. 80704D.
Chemical Abstracts, vol. 99, No. 25, Dec. 19, 1983, Columbus, Ohio, USA, Abstract No. 212722F.
Chemical Abstracts, vol. 70, No. 7, Feb. 17, 1969, Columbus, Ohio, USA, Abstract No. 29070D.

Primary Examiner—Johann Richter
Attorney, Agent, or Firm—Foley & Lardner

[57] ABSTRACT

Pharmacologically active compounds corresponding to the formula I $$R^3-Z-(CH_2)_n-\overset{R^1}{\underset{|}{N}}-(CH_2)_m-R^2$$

in which
n represents 2-5,
m represents 2-6,
$R^1$ denotes hydrogen or lower alkyl,
$R^2$ represents an $OR^4$ group in which $R^4$ denotes lower alkyl or a phenyl or phenyl-lower alkyl group which is optionally substituted in the phenyl ring, or
$R^2$ represents a $$-N\begin{matrix}R^5\\R^6\end{matrix}$$

group in which
$R^5$ and $R^6$ independently of one another each denote hydrogen, lower alkyl or a phenyl or phenyl-lower alkyl group which is optionally substituted in the phenyl ring, or
$R^5$ and $R^6$, together with the nitrogen atom to which they are bonded, represent a saturated 5- or 6-membered heterocycle,
$R^3$ represents a saturated monocyclic or bicyclic hydrocarbon group which is derived from terpenes and has 10 or 11 carbon atoms, and
Z represents oxygen or, if $R^3$ is a dihydronopyl group, Z may also represent sulfur,
and salts thereof.

7 Claims, No Drawings

ALKYLAMINOALKYLAMINE AND ETHER COMPOUNDS, PROCESSES AND INTERMEDIATES FOR THEIR PREPARATION, AND MEDICAMENTS CONTAINING THEM

FIELD OF THE INVENTION

The present invention relates to novel dialkylamine derivatives, which contain an alkyl radical substituted by an alkoxy or alkylthio group containing a monocyclic or bicyclic hydrocarbon radical and an alkyl radical carrying an amine or ether function, and to pharmaceutical preparations containing these compounds and processes and intermediates for preparing such compounds.

SUMMARY OF THE INVENTION

It is an object of the present invention to prepare novel dialkylamino compounds having useful pharmacological properties.

It has now been found that the novel alkylaminoalkylamine and ether compounds, which are substituted on the alkyl radical by alkyloxy or alkylthio groups and which contain monocyclic or bicyclic hydrocarbon radicals derived from terpenes, have useful pharmacological properties and in particular have a favorable pharmacological action in the gastrointestinal tract. They are distinguished in particular by gastrointestinally active spasmolytic properties and have good tolerability and low toxicity. In addition, they also have gastro-protective and ulcer-inhibiting properties.

The present invention therefore relates to novel dialkylamino compounds of the general formula I

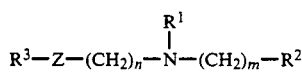

wherein
n represents 2-5,
m represents 2-6,
$R^1$ denotes hydrogen or lower alkyl,
$R^2$ represents an $OR^4$ group in which $R^4$ denotes lower alkyl or a phenyl or phenyl-lower alkyl group which is optionally substituted in the phenyl ring by 1 to 3 substituents selected from the group consisting of lower alkyl, lower alkoxy, halogen and lower alkylenedioxy, or
$R^2$ represents a

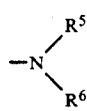

group in which
$R^5$ denotes hydrogen, lower alkyl or a phenyl or phenyl-lower alkyl group which is optionally substituted in the phenyl ring by to 1 to 3 substituents from the group of lower alkyl, lower alkoxy, halogen, trifluoromethyl and lower alkylenedioxy, and
$R^6$ denotes hydrogen, lower alkyl or a phenyl or phenyl-lower alkyl group which is optionally substituted in the phenyl ring by 1 to 3 substituents selected from the group consisting of lower alkyl, lower alkoxy, halogen, trifluoromethyl and lower alkylenedioxy, or $R^5$ and $R^6$, together with the nitrogen atom to which they are bonded, represent a saturated 5- or 6-membered heterocycle, which can optionally contain a second hetero atom from the group of oxygen and $N-R^7$, in which $R^7$ denotes lower alkyl or benzyl,
$R^3$ represents a saturated monocyclic or bicyclic terpene hydrocarbon radical having 10 carbon atoms or a bicyclic hydrocarbon radical having 11 carbon atoms, corresponding to the formula b

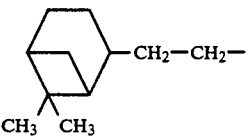

and
Z represents oxygen or, if $R^3$ denotes a group of formula b, Z may also represent sulfur,
and their physiologically acceptable acid addition salts.

DETAILED DESCRIPTION OF PREFERRED EMBODIMENTS

In the compounds of formula I, $R^1$ can denote hydrogen or preferably lower alkyl. A lower alkyl group $R^1$ can be straight-chain or branched and can contain 1 to 4 carbon atoms and in particular represents the methyl group.

The group $R^2$ in the compounds of the formula I may represent an oxy radical $OR^4$ or an amino radical $NR^5R^6$. If the substituents $R^4$, $R^5$ and/or $R^6$ represent lower alkyl groups, these can be straight-chain or branched and can contain 1 to 4 carbon atoms. If the group $R^2$ contains a phenyl group, this can be attached directly or via a lower alkylene chain, which can contain 1 to 3, in particular 1 or 2, carbon atoms, to the oxygen or nitrogen atom of the radical $R^2$. The phenyl group can be unsubstituted or it may be substituted by 1 to 3 substituents selected from the group consisting of lower alkyl, lower alkoxy, lower alkylenedioxy, halogen and trifluoromethyl. Lower alkyl or alkoxy substituents on the phenyl group can be straight-chain or branched and can contain 1 to 4, in particular 1 or 2 carbon atoms and preferably represent methyl or methoxy. Lower alkylenedioxy groups contain 1 or 2 carbon atoms and are bonded to two adjacent carbon atoms of the phenyl group. For multiple substitution of the phenyl group, methoxy and methylenedioxy are particularly suitable. Suitable halogen substituents on the phenyl group particularly include fluorine, chlorine or bromine. Particularly advantageous compounds include, for example, those in which $R^2$ represents an amino group $NR^5R^6$ in which the substituents $R^5$ and $R^6$ can be independent of one another or alternatively $R^5$ and $R^6$, together with the nitrogen atom to which they are bonded, form a heterocycle. If such a heterocycle contains a second hetero member, it is preferably oxygen. If the hetero member is an imino group $NR^7$, $R^7$ preferably denotes a lower alkyl group, for example an alkyl group having 1 to 4 carbon atoms, in particular methyl. If the substituents $R^5$ and $R^6$ denote radicals which are independent of one another, it is advantageous if at least one of these substituents is a phenylalkyl group having 1 or 2 carbon atoms in the alkylene chain and which is optionally substituted in the phenyl ring. The second substituent can advantageously be a lower alkyl group or also a phenyl- $C_1$ or $C_2$ alkyl group which is optionally substituted in the phenyl ring.

The alkylene chain 13 $(CH_2)_m$— can contain 2 to 6, preferably 2 or 3, members. The alkylene chain —$(CH_2)_n$— can contain 2 to 5, in particular 2 or 3, members. Z preferably represents oxygen.

The hydrocarbon radicals $R^3$ of the compounds of formula I are radicals derived from terpenes and having 10 or 11 carbon atoms, which can contain 17 to 19 hydrogen atoms. There are several asymmetric centers in each of the radicals, each of which can have the R- or S-configuration, so that the compounds can exist in several diastereoisomeric forms. The invention includes both the individual stereoisomeric forms of the compounds of formula I and mixtures thereof. Preferably, the compounds of the formula I contain hydrocarbon radicals $R^3$ which are derived from naturally occurring terpene derivatives, or which can be prepared from these. In nature, terpene derivatives, for example saturated terpene alcohols, exist in plants as more or less sterically pure substances or as stereoisomer mixtures of varying composition. Accordingly, commercially available terpene derivatives, which are generally prepared from natural products, also exist in more or less sterically pure form or as stereoisomer mixtures. The present invention contemplates within its scope, in particular, those compounds of formula I in which the hydrocarbon radical $R^3$ is derived from natural and/or commercially available terpene derivatives.

In the preparation of compounds of the formula I according to the invention, the configuration of the hydrocarbon radical $R^3$ of the starting compound $R^3$-Z-H is retained, so that, depending on the starting material employed, stereoisomer mixtures or more or less stereoisomerically pure substances of formula I are obtained as final products.

Suitable hydrocarbon radicals $R^3$ include in particular monocyclic or bicyclic hydrocarbon radicals having 10 or 11 carbon atoms selected from the group consisting of:

1-methyl-4-isopropylcyclohex-3-yl (=menthyl) of formula a

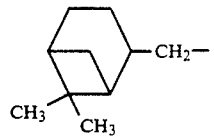

a 2-(6,6-dimethylbicyclo[3.1.1]hept-2-yl)ethyl (=dihydronopyl) of formula b

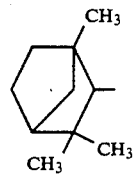

b 6,6-dimethylbicyclo[3.1.1]hept-2-ylmethyl (=myrtanyl) of formula c

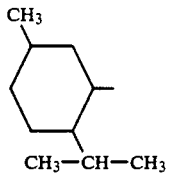

c 1,3,3-trimethylbicyclo[2.1.1]hept-2-yl (=fenchyl) of formula d

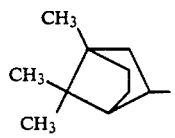

d and 1,7,7-trimethylbicyclo[2.2.1]hept-2-yl (=bornyl) of formula e

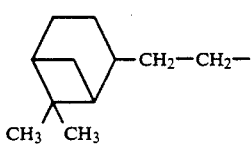

e

Among the above-mentioned radicals $R^3$, the 1-methyl-4-isopropylcyclohex-3-yl radical of the formula a (=menthyl radical) is especially suitable. This radical, which is derived from menthol, contains asymmetric centers in positions 1, 3 and 4 of the cyclohexyl structure, which each can have the R- or the S- configuration. In nature, the two enantiomericforms, 1R,3R,4S-1-methyl-4-isopropylcyclohexan-3-ol (=L-menthol) and 1S,3S,4R-1-methyl-4-isopropylcyclohexan-3-ol (=D-menthol) occur most frequently. Among the possible menthyl-substituted compounds of the formula I, these two menthyl forms are preferred in the present invention, particularly the L-menthyl form or stereoisomer mixtures in which the L-menthyl form predominates.

Furthermore, the 2-(6,6-dimethylbicyclo-[3.1.1]hept-2-yl)ethyl radical of the formula b (=dihydronopyl radical) is very suitable as the hydrocarbon radical $R^3$. This radical contains asymmetric centers in positions 1, 2 and 5 of the bicycloheptane ring structure, which each can have the R- or S-configuration. Within the scope of the present invention, a 2-(6,6-dimethylbicyclo[3.1.1]hept-2-yl)ethyl group is preferred which originates from a terpene alcohol derived from natural (—)-β-pinene (=1S,5S)-(—)-6,6-dimethyl-2-methylenebicyclo-[3.1.1]heptane) in which the asymmetric centers in the 1- and 5-positions have the S-configuration. Accordingly, in the 2-(6,6-dimethylbicyclo[3.1.1]-hept-2-yl)ethyl derivatives of formula I, the asymmetric centers in the 1- and 5-positions of the terpene ring structure also have the S-configuration, while the asymmetric center in the 2-position can have either the S- or the R-configuration, so that the corresponding substances of the formula I can occur in two diastereomeric forms. Of these two dihydronopyl forms, the cis form, in which the asymmetric center in position 2 of the bicycloheptane ring structure has the S-configuration, or mixtures in which this form is present to a predominant extent, are particularly preferred.

Suitable hydrocarbon radicals $R^3$ also include the 1,3,3-trimethylbicyclo[2.1.1]hept-2-yl radical of formula d (=fenchyl radical) and the 1,7,7-trimethylbicyclo[2.2.1]hept-2-yl radical of formula e (=bornyl radical).

In the fenchyl radical $R^3$, asymmetric centers, which each may have the R- or the S-configuration, are present in positions 1, 2 and 4 of the bicycloheptane ring structure. Within the scope of the present invention, fenchyl radicals are preferred which are derived from natural (+)-fenchol in which a 1S,4R-configuration is present, while the asymmetric center in the 2-position can preferably have the R-configuration, but also may have the S-configuration.

The bornyl radical $R^3$ contains asymmetric centers in positions 1, 2 and 4 of the bicycloheptane ring structure, which each may have the R- or the S-configuration. In natural bornyl derivatives, the endobornyl radical mainly occurs. The (−)-form (=1S,2R,4S-form) predominates over the (+)-form (=1R,2S,4R-form). Within the scope of the present invention, preferred bornyl derivatives are those in which the bornyl radical originates from natural borneol and in which the 1S,2R,4S-form is present, or mixtures in which this form is present to a predominant extent.

If $R^3$ is a 6,6-dimethylbicyclo[3.1.1]hept-2-ylmethyl radical of the formula c (=myrtanyl radical), the configuration derived from natural (−)-β-pinene is preferably present in which the asymmetric centers in the 1-and 5-positions have the S-configuration.

The novel dialkylamino compounds of formula I are distinguished by interesting pharmacological properties. In particular, the compounds exhibit a regulating action on the motility of the gastrointestinal tract and are capable of acting against motility disorders, in particular of the colon. Thus, in an experiment with isolated organs from the gastrointestinal tract, induced spasms were lysed under the influence of these compounds, and in an animal experiment, in vivo colon amplitudes were damped.

A. Determination of the spasmolytic action in vitro.

In a physiological saline solution, isolated organ strips from the gastrointestinal tract such as gastric fundus, gastric antrum, duodenum, ileum, proximal colon and distal colon react to the addition of a spasmogen, for example potassium chloride solution, by contracting. This contraction of the organ strips, induced by the addition of spasmogen, is decreased by addition of the compounds of the invention. The extent of the regression of the contraction is an index of the spasmolytic activity of the compounds. Determination of spasmolytic activity against potassium chloride-induced spasms in isolated guinea pig ileum.

Female guinea pigs of the Wiga strain having a body weight of about 300 g were sacrificed. Organ strips from the ileum about 1 cm long were placed in an organ bath of Tyrode solution at 37° C. and mounted in a conventional apparatus for the isotonic measurement of changes in length. Tyrode solution is an aqueous solution containing 136.9 mmol of NaCl, 2.68 mmol of KCl, 2.31 mmol of $CaCl_2$, 1.0 mmol of $MgCl_2$, 11.9 mmol of $NaHCO_3$, 1.45 mmol of $NaH_2PO_4$ and 5.55 mmol of glucose per liter. After an equilibration phase of one hour, 50 mmol/l of potassium chloride were added to the bath fluid to test the sensitivity of the ileum strips. The strips were then rinsed again with Tyrode solution. 50 mmol/l of potassium chloride were then added to the bath fluid again to induce a contraction of the ileum strip due to spasm. As soon as the contraction of the ileum strip due to spasm has reached a constant maximum value, the test substance was added to the bath fluid, and the decrease in the contraction was recorded and calculated as a % of the constant maximum contraction.

The following table A gives the obtained by the test method described above. The example numbers given in the table for the compounds of formula I correspond to the numbers of the subsequent Preparation Examples. In Table A, the $EC_{50}$ represents the concentration of the test substance in moles/liter in the bath fluid with which an approximately 50% reduction is achieved in the strength of the maximum spasmodic contraction induced in the ileum strip by potassium chloride.

TABLE A

| Example No. | Spasmolytic action in vitro against potassium-induced contraction on the isolated guinea pig ileum | |
|---|---|---|
| | $EC_{50}$ | in mol/l |
| 1 | 12 | $\times 10^{-6}$ |
| 2 | 2.0 | $\times 10^{-6}$ |
| 7 | 16 | $\times 10^{-6}$ |
| 10 | 30 | $\times 10^{-6}$ |
| 16 | 4.9 | $\times 10^{-6}$ |
| 19 | 0.54 | $\times 10^{-6}$ |
| 20 | 7.9 | $\times 10^{-6}$ |
| 21 | 3.6 | $\times 10^{-6}$ |
| 22 | 8.7 | $\times 10^{-6}$ |
| 23 | 1.5 | $\times 10^{-6}$ |
| 24 | 14 | $\times 10^{-6}$ |
| 32 | 20 | $\times 10^{-6}$ |
| 34 | 47 | $\times 10^{-6}$ |
| 35 | 1.9 | $\times 10^{-6}$ |
| 36 | 43 | $\times 10^{-6}$ |
| 37 | 26 | $\times 10^{-6}$ |
| 38 | 19 | $\times 10^{-6}$ |
| 44 | 2.4 | $\times 10^{-6}$ |
| 46 | 4.8 | $\times 10^{-6}$ |
| 48 | 0.68 | $\times 10^{-6}$ |
| 50 | 1.3 | $\times 10^{-6}$ |

B. Determination of in vivo activities on spontaneous motility in the gastrointestinal tract.

The effects of the test substances on the amplitudes and frequencies of gastric and intestinal contractions were measured by the following experimental method. Determination of the activity of the test substances on the spontaneous motility of the colon in anesthetized rats.

Fasting rats of the SIV 50 strain having a body weight of 180–250 g were anesthetized with a ketamine/xylazine mixture. The animals were tracheotomised and laparotomised. After applying a pylorus ligature, a stomach tube was inserted into the stomach and connected at the other end to a calibrated pressure transducer (Statham element P 23 ID) via a three-way tap. A corresponding tube was inserted rectally 8 to 9 cm into the colon and likewise connected, in the same manner, to a corresponding calibrated pressure transducer. The stomach of the animals was then filled with 2 to 3 ml of water via the tube. The pressure variations in the colon were recorded before and after administration of the test substances using a Watanabe multicorder (MC 641). The differences between the average amplitudes before and after the treatment were determined, and the percent change in the average amplitudes caused by the test substances relative to the values obtained before the treatment is reported in the following Table B.

C. Determination of the minimum toxic dose.

Male mice weighing 20-25 g were orally administered maximum doses of 300 mg/kg of the test substance. The animals were carefully observed for toxic symptoms for three hours. All symptoms and deaths over a period of 24 hours after administration were also recorded. Accompanying symptoms were likewise observed and recorded. If death or strongly toxic symptoms was observed, increasingly smaller doses were administered to further mice until toxic symptoms no longer occurred. The lowest dose which caused death or strongly toxic symptoms is given as the minimum toxic dose in the following Table B.

TABLE B

| Example No. | Action on spontaneous motility in the colon of the rate at a dose of 100 μmol/kg i.p. % amplitude reduction | Minimum toxic dose in the mouse mg/kg p.o. |
|---|---|---|
| 1 | 55 | >300 |
| 2 | 55 | >300 |
| 19 | 74 | — |
| 20 | 69 | >300 |
| 21 | 62 | 300 |
| 22 | 85 | 100 |
| 48 | 85 | — |

In addition to their spasmolytic activity on the gastrointestinal tract, the compounds also exhibit a protective effect on the gastrointestinal mucosa, in particular ulcer-inhibiting properties.

Due to their activity in the gastrointestinal tract, the compounds of formula I are useful in gastroenterology as medicaments for prophylaxis and treatment of spasms in the gastrointestinal tract of larger mammals, particularly humans. Thus, the substances are suitable, for example, for treating functional motility disorders of the gastrointestinal tract with symptoms such as nausea, stomach pains, intestinal cramps or cramps of other intestinal organs, and irritable bowel syndrome.

The doses to be used may vary between individuals and naturally can vary depending on the condition to be treated, the substance used, and the form of administration. For example, parenteral formulations will generally contain a smaller amount of active ingredients than oral preparations. In general, however, pharmaceutical forms having an active ingredient content of 10 to 200 mg per individual dose are suitable for administration to larger mammals, in particular humans.

As medicines, the compounds of formula I may be admixed with customary pharmaceutical adjuvants in pharmaceutical preparations such as, for example, tablets, capsules, suppositories or solutions. These pharmaceutical preparations can be produced by known methods using customary solid excipients such as, for example, lactose, starch or talc or liquid diluents such as, for example, water, fatty oils or liquid paraffins, and using customary pharmaceutical adjuvants, for example tablet disintegrators, solubilizers or preservatives.

According to the invention, the novel compounds of formula I and their acid addition salts are obtained by a process in which a) for preparing compounds of the formula Ia $$R^3-Z-(CH_2)_n-\overset{R^1}{\underset{|}{N}}-(CH_2)_m-R^2$$

in which n, m, $R^1$, $R^3$ and Z have the above meanings and $R^{1'}$ denotes lower alkyl, compounds of the formula II $$R^3-Z-(CH_2)_n-\overset{R^{1'}}{\underset{|}{N}}-(CH_2)_m-X$$

in which n, m, $R^1$, $R^3$ and Z have the above meanings and X represents a removable leaving group Y or, for preparing those compounds in which $R^2$ represents an $OR^4$ group, X can also represent hydroxyl, are reacted with compounds of formula III $$H-R^2$$

in which $R^2$ has the above meaning, or if X is hydroxyl, also with a compound of formula III'

$$Y-R^4$$

in which $R^4$ has the above meaning and Y represents a removable leaving group, or b) for preparing compounds of formula I, compounds of formula IV $$R^3-Z-(CH_2)_{n-1}-CO-\overset{R^1}{\underset{|}{N}}-(CH_2)_{m-1}-D$$

in which n, m, $R^1$, $R^3$ and Z have the above meanings and D represents a $CH_2$-$N_3$ group, an $R^2$-$CH_2$ group in which $R^2$ has the above meaning, or an $$\overset{O}{\underset{\|}{C}}-N\diagup\overset{R^5}{\diagdown R^6} \text{ group; or}$$

c) for preparing compounds of formula Ib $$R^3-Z-(CH_2)_n-\overset{R^1}{\underset{|}{N}}-(CH_2)_m-R^{2'}$$

in which n, m, $R^1$, $R^3$ and Z have the above meanings and $R^{2'}$ has the meaning given for $R^2$ with the exception of groups containing an NH function, compounds of formula V $$R^3\text{-}Z\text{-}(CH_2)_n\text{-}Q$$

in which n, $R^3$ and Z have the above meanings and Q represents a $$-N\diagup\overset{R^{1'}}{\diagdown H}$$

group in which $R^{1'}$ has the above meaning, or Q represents a cleavable leaving group Y, are reacted with compounds of formula VI $$Q'\text{-}(CH_2)_m\text{-}R^{2'}$$

in which m and R²' have the above meanings and Q' represents a cleavable leaving group Y if Q is a

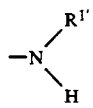

group, or Q' represents a

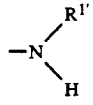

group if Q is a cleavable leaving group Y; or d) for preparing compounds of the general formula Ic

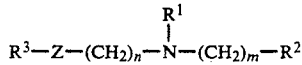

in which R¹', R²', R³ and Z have the above meanings and n' and m' have the meanings given for n and m, except, however, if R²' represents an NR⁵R⁶ group, the sum of n' and m' must be other than 4, compounds of formula VII

in which R³ and Z have the above meanings, are reacted with compounds of formula VIII

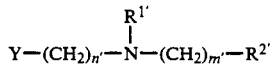

in which n', m', R¹', R²', and Y have the above meanings, or e) for preparing compounds of the formula Id

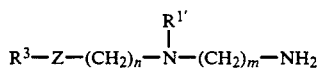

in which n, m, R¹', R³ and Z have the above meanings, the group A in compounds of formula IX

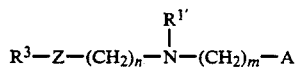

in which n, m, R¹', R³ and Z have the above meanings and A denotes an azide or phthalimide radical, is converted into a NH₂ group, or f) for preparing compounds of the formula Ie

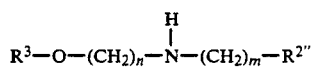

in which n, m and R³ have the above meanings and R²'' has the meaning given for R² with the exception of radicals containing an optionally substituted benzyl group, the group B in compounds of the general formula X

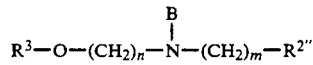

in which n, m, R²' and R³ have the above meanings and B represents a group which is removable by hydrogenolysis, is removed by hydrogenolysis, and if desired, in resulting compounds of the general formula I, in which R¹ denotes hydrogen, a lower alkyl radical R¹' or, in resulting compounds of the formula I in which R² contains a free NH function, a lower alkyl radical R⁵' which is optionally substituted by a phenyl group which is optionally substituted by 1 to 3 substituents selected from the group consisting of lower alkyl, lower alkoxy, halogen, trifluoromethyl and lower alkylenedioxy, is introduced and, if desired, free compounds of formula I are converted into corresponding acid addition salts or an acid addition salt of a compound of formula I is converted into the corresponding free compound.

The reaction of compounds of formula II with compounds of formula III according to process variant a) can be carried out in a known manner under customary conditions for alkylating amines or alcohols. Suitable leaving groups Y in the compounds of formula II or the compounds of formula III' are preferably halogens such as chlorine, bromine or iodine or alternatively organic sulfonic acid radicals, for example radicals of lower alkanesulfonic acids such as, for example, methanesulfonic acid, or of aromatic sulfonic acids such as benzenesulfonic acid or benzenesulfonic acids substituted by lower alkyl or halogen, for example toluenesulfonic acid or bromobenzenesulfonic acid. The reaction is advantageously carried out in solution under basic conditions. Solvents which can be used are inert organic solvents or alternatively an excess of a compound of the formula III. Suitable inert organic solvents include lower alcohols, dimethylformamide, acetonitrile, or ethers, particularly cyclic ethers such as tetrahydrofuran, or aromatic hydrocarbons such as benzene or toluene, or mixtures of the above-mentioned solvents. If the compound of formula III is a lower alcohol, aprotic solvents are preferably employed. An excess of this alcohol, optionally mixed with water, can also be used as the solvent. Advantageously, the reaction is carried out in the presence of an at least equivalent amount of an acid-binding base. Examples of suitable bases for the aminoalkylation include alkali metal carbonates, alkali metal hydroxides, and tertiary organic bases, in particular tertiary lower alkylamines such as triethylamine or N,N-dimethylaminopyridine or, if desired, also an excess of an amine of the formula III. If m is 2 in the compounds of formula II, then an aziridine ring is formed under the reaction conditions by intramolecular ring closure, and reacts with the compounds of the formula III even in the presence of relatively mild bases and at comparatively low temperatures. If primary amines or ammonia are used as compounds of the formula III, it is advantageous to employ a multiple excess of these compounds of formula III in order to avoid side reactions. For ether formation, it is advantageous to employ strong bases such as alkali metals, or alkali metal amides, hydrides, hydroxides or alkoxides and to first convert the alcohol of formula II or III into the corresponding alkoxide by reaction with one of the above-mentioned strong bases and to then react the alkoxide further. The reaction temperature may vary depending on the nature of the reagents used and can range from 0° C. to the boiling temperature of the solvent, preferably between about 20° C. and the boiling temperature of the solvent. Depending on the nature of the reaction conditions chosen, the reaction time can be between 2 and 12 hours.

The reduction of amides of formula IV according to process variant b) can be carried out in a known manner with reducing agents suitable for reducing amides. Particularly suitable reducing agents include complex metal hydrides such as lithium aluminium hydride, diborane, sodium borohydride in glacial acetic acid, or diisobutylaluminium hydride. The reaction is carried out in a solvent which is inert under the reaction conditions, for example a preferably cyclic ether such as tetrahydrofuran. The reaction temperature can range from room temperature to the boiling temperature of the solvent. Depending on the nature of the reducing agent used and the reaction conditions chosen, the reaction time can be between 3 and 10 hours.

The reaction of compounds of formula V with compounds of formula VI according to process variant c) can be carried out by customary aminoalkylation methods. Thus, the reaction can be carried out, for example, under the conditions given for reacting compounds of formula II with compounds of formula III.

The reaction of compounds of formula VII with compounds of formula VIII according to process variant d) can be carried out in a known manner according to customary methods for ether or thioether formation. Thus, the compounds of formula VII are advantageously reacted with compounds of formula VIII in an organic solvent which is inert under the reaction conditions and in the presence of a strong base which is capable of reacting with the alcohols or thioalcohols of formula VII to give the corresponding alkoxides or thioalkoxides. Suitable strong bases include, for example, alkali metals, alkali metal hydrides, alkali metal amides or alkali metal hydroxides. Suitable inert organic solvents include, for example, ethers, particularly cyclic ethers such as tetrahydrofuran or dioxane, or aromatic hydrocarbons such as benzene, toluene or xylene. If desired, the reaction of compounds of formula VII with compounds of formula VIII can also be carried out without addition of a solvent. The reaction temperature can range from room temperature to boiling temperature of the reaction mixture, and depending on the reaction conditions, the reaction time can be between 2 and 10 hours.

The preparation of amine compounds of formula Id from corresponding azides or phthalimides of formula IX according to process variant e) can be carried out in a known manner by customary methods for liberating amines from corresponding azides or phthalimides. Thus, for example, phthalimides of formula IX can be cleaved by treating them in a known manner with hydrazine to give compounds of formula Id. Azides of the formula IX can be converted into amine compounds of formula Id in a known manner by treating them with a complex metal hydride, for example lithium aluminium hydride, or if Z represents oxygen, by catalytically hydrogenating them, for example using a palladium/carbon catalyst.

The preparation of compounds of formula Ie from compounds of formula X according to process variant f) can be carried out by catalytic hydrogenolysis in a known manner. Suitable groups B which are removable by hydrogenolysis include, in particular, the benzyl group or benzyl groups which are substituted in the phenyl ring. Hydrogenolysis can be carried out in the presence of catalysts suitable for hydrogenolytic debenzylation at a hydrogen pressure of 1 to 10 bar, particularly 1–6 bar, and at temperatures of from 0° C. to 60° C. in a solvent which is inert under the reaction conditions. Suitable catalysts include, for example, palladium on carbon, palladium hydroxide on carbon, or Raney nickel. Suitable solvents include, for example, lower alcohols such as ethanol, ethyl acetate, acetic acid, aromatic hydrocarbons such as toluene, or mixtures thereof, if desired also mixed with water. Advantageously, the hydrogenolysis is carried out in acidified medium, for example in a reaction medium containing added hydrochloric acid.

Compounds of the formula I in which $R^1$ denotes hydrogen or in which $R^1$ denotes lower alkyl and in which $R^2$ contains a free NH function, can subsequently be alkylated in a known manner, if desired, to give corresponding N-substituted compounds. Suitable alkylating agents include compounds $R^{1'}$-Y or $R^{5'}$-Y in which $R^{1'}$, $R^{5'}$ and Y have the above meanings, in particular $R^{1'}$ halides and $R^{5'}$ halides, especially iodides, or sulfates or sulfonic acid esters. Advantageously, the alkylation is carried out in an organic solvent which is inert under the reaction conditions and in the presence of a base such as, for example, an alkali metal carbonate or a tertiary organic amine, in particular a tertiary lower alkylamine. Depending on the base used, suitable solvents include dimethylformamide, acetonitrile, cyclic ethers such as tetrahydrofuran or dioxane, aromatic hydrocarbons such as toluene, or alternatively lower alcohols. The reaction can be carried out at temperatures between room temperature and the boiling temperature of the solvent. Subsequent alkylation can also be carried out as a reductive alkylation in a known manner by reacting with an appropriate aldehyde, in particular formaldehyde, under reducing conditions. For example, the compounds can be reacted with the aldehyde in the presence of a reducing agent, for example formic acid. If Z represents oxygen in the compounds of formula I and the compounds do not contain any radicals which are removable by hydrogenolysis, the reductive alkylation can also be carried out by reacting the compound with the aldehyde and catalytically hydrogenating the reaction mixture. Suitable hydrogenation catalysts include, for example, palladium on carbon or Raney nickel. When an alkyl group $R^{1'}$ is introduced, any free NH function in the group $R^2$ will also be alkylated.

The compounds of the formula I can be isolated from the reaction mixture in a known manner and purified. Acid addition salts can be converted into free bases in a customary manner and the free bases can be converted, if desired, into pharmacologically acceptable acid addition salts in a known manner.

If desired, the individual stereoisomeric forms can be concentrated and isolated from mixtures of stereoisomeric compounds of formula I by conventional separation methods, for example, by fractional crystallization of suitable salts or by chromatographic methods.

Suitable pharmacologically acceptable acid addition salts of the compounds of the formula I include, for example, their salts with inorganic acids, for example hydrohalic acids, particularly hydrochloric acid, sulfuric acid or phosphoric acids, or with organic acids, for example lower aliphatic monocarboxylic or dicarboxylic acids such as maleic acid, fumaric acid, oxalic acid, lactic acid, tartaric acid or acetic acid, or sulfonic acids, for example lower alkanesulfonic acids such as methanesulfonic acid or benzenesulfonic acids which are optionally substituted in the benzene ring by halogen or lower alkyl, such as p-toluenesulfonic acid, or cyclohexylaminosulfonic acid.

The starting compounds of the formula II can be obtained in known manner. Compounds of formula IIa

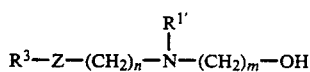

in which $R^{1'}$, $R^3$, Z, n and m have the above meanings, can be obtained in a known manner by reducing amides of formula XIa

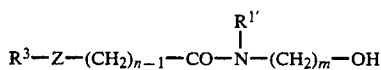

in which $R^{1'}$, $R^3$, Z, n and m have the above meanings. The reduction can be carried out, for example, under the conditions given above for reducing compounds of formula IV. Compounds of formula IIb

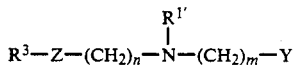

in which $R^{1'}$, $R^3$, Z, n, m and Y have the above meanings, can be obtained from compounds of formula IIa by converting the hydroxyl group in the compounds of formula IIa into a leaving group Y in a known manner. Thus, the compounds of formula IIa can be reacted in a known manner with thionyl chloride or with phosphorus halides, for example, to introduce a halogen Y. Sulfonic acid radicals Y can be introduced by acylating compounds of formula IIa with an appropriate sulfonyl halide in a known manner.

Compounds of the formula II can also be obtained by reacting compounds of formula Va

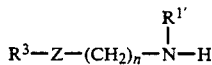

in which $R^{1'}$, $R^3$, Z and n have the above meanings, with compounds of formula XII

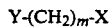

in which Y, m and X have the above meanings. The reaction can be carried out by customary aminoalkylation methods, for example under the conditions given above for reacting compounds of formula II with compounds of formula III. To avoid side reactions, it is advantageous to employ an excess of the compound of formula XII. If X in the compound of formula XII is a leaving group Y, it is advantageous if the two leaving groups present in the compound of formula XII have different reactivities in order to avoid simultaneous reaction of both leaving groups with compounds of formula Va.

Compounds of the formula IIa can also be obtained by reacting an amine of formula XIIIa

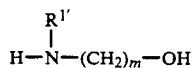

in which $R^{1'}$ and m have the above meanings, with compounds of formula Vb

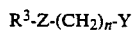

in which $R^3$, Z, n and Y have the above meanings. The reaction can be carried out by customary aminoalkylation methods, for example analogously to the reaction of compounds of formula V with compounds of formula VI.

Amides of the formula XIa can be obtained by reacting acids of formula XIV

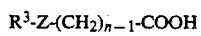

in which $R^3$, Z and n have the above meanings, with amines of formula XIIIa in a known manner. Thus, reactive derivatives of the acids of formula XIV, particularly the acid halides (preferably chlorides), esters and mixed anhydrides, can be reacted with the amines of formula XIIIa by customary methods for forming amide groups by aminoacylation. The aminoacylation can be carried out in a solvent which is inert under the reaction conditions and at temperatures from room temperature to the boiling temperature of the solvent. Suitable solvents include halogenated hydrocarbons such as dichloromethane or chloroform, aromatic hydrocarbons such as benzene, toluene, xylene or chlorobenzene, cyclic ethers such as tetrahydrofuran or dioxane, dimethylformamide or mixtures of these solvents. The aminoacylation can optionally be carried out, particularly if an acid halide or mixed anhydride is used, in the presence of an acid-binding reagent. Particularly suitable acid-binding agents include organic bases, for example tertiary lower alkylamines or pyridines. If acid halides are employed, the reaction can also be carried out in a known manner by the Schotten-Baumann method in an aqueous medium and in the presence of an inorganic base. If the acid itself is employed, the reaction is advantageously carried out in the presence of a suitable coupling reagent known from peptide chemistry. Particular examples of suitable coupling reagents, which promote amide formation by reacting with the free acid in vitro to form a reactive acid derivative, include alkylcarbodiimides, preferably cycloalkylcarbodiimides such as dicyclohexylcarbodiimide, or N-lower alkyl-2-halopyridinium salts, particularly halides or tosylates, preferably N-methyl-2-chloropyridinium iodide (see, for example, Mukayama in Angew. Chemie 91, 789 to 912). The reaction in the presence of a coupling reagent can be carried out, for example, at temperatures from $-30°$ C. to $+100°$ C. using solvents such as halogenated hydrocarbons and/or aromatic solvents in the presence of an acid-binding amine.

Acids of formula XIV can be obtained by reacting compounds of formula VII with halocarboxylic acids of formula XV

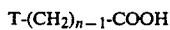

in which n has the above meaning and T represents halogen. The reaction of compounds of formula VII with acids of formula XV can be carried out in a known manner under customary reaction conditions for forming ethers or thioethers. Thus, salts of the acids of formula XV can be reacted with alkali metal salts of compounds of formula VII under basic conditions. The reaction can be carried out, for example, under the conditions given for reacting compounds of formula VII with compounds of formula VIII.

The compounds of formula IV can be obtained starting from acids of formula XIV. Thus, acids of formula XIV can be reacted with compounds of formula VI'

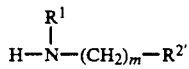

in which $R^1$, $R^{2'}$ and m have the above meanings, to give compounds of formula IV in which D is an $R^{2'}$-$CH_2$ group, or acids of formula XIV can be reacted with compounds of formula XVI

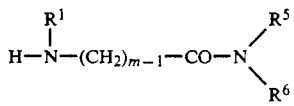

in which $R^1$, $R^5$, $R^6$ and m have the above meanings, to give compounds of formula IV in which D is a $CO-NR^5R^6$ group. The reactions can be carried out by customary aminoacylation methods, for example under the reaction conditions given for the reaction of acids of formula XIV with amines of formula XIIIa Compounds of formula IV in which D is a $CH_2-N_3$ group or a $CH_2-NH_2$ group can be obtained starting from amides of formula XI

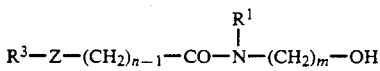

in which $R^1$, $R^3$, Z, n and m have the above meanings. For this purpose, the hydroxyl group of the compound of formula XI is first converted in a known manner to a functional group Y. The reaction product is then reacted in a known manner with an alkali metal azide, or the product is first reacted with an alkali metal phthalimide, and the phthalimide is then cleaved to give the $NH_2$ group.

Amides of formula XI can be obtained by reacting acids of formula XIV with amines of formula XIII

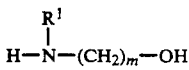

in which $R^1$ and m have the above meanings, under customary aminoacylation conditions.

Compounds of formula XVI can be obtained by reacting a reactive acid derivative of a halocarboxylic acid of formula XVII

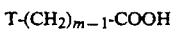

in which T and m have the above meanings, with an amine of formula IIIa

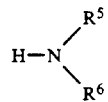

in which $R^5$ and $R^6$ have the above meanings, by customary methods for forming an amide group to give an amide of formula XVIII

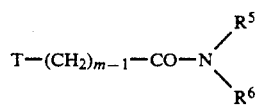

in which $R^5$, $R^6$, m and T have the above meanings, and then further reacting this amide with an amine of formula XIX

in which $R^1$ has the above meaning. If T represents chlorine, it is advantageously first replaced by iodine in a known manner. It is desirable to use a multiple excess of amine in order to avoid side reactions.

Compounds of formula Va can be obtained by reducing amides of formula XX

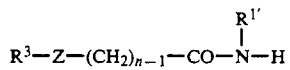

in which $R^{1'}$, $R^3$, Z and n have the above meanings. The reduction can be carried out in a known manner, for example under the conditions given for reducing compounds of formula IV.

Amides of formula XX can be obtained by reacting reactive acid derivatives of acids of formula XIV with amines of formula XIXa

in which $R^{1'}$ has the above meaning, under customary conditions for forming amides.

Compounds of the general formula Va'

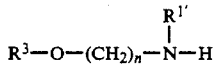

in which $R^{1'}$, $R^3$ and n have the above meanings, can also be obtained by hydrogenolysis of compounds of formula XXI

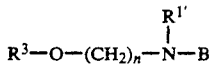

in which $R^{1'}$, $R^3$, n and B have the above meanings, especially by hydrogenolytic debenzylation of compounds of formula XXI in which B is benzyl. The hydrogenolysis can be carried out under the conditions given for hydrogenolysis of compounds of formula X.

Compounds of formula Vb can be obtained by reacting an alkali metal salt of a compound of formula VII in a known manner with a compound of formula XXII T-(CH$_2$)$_n$-X in which T, n and X have the above meanings, and if X is a hydroxyl group, then converting this in a known manner into a leaving group Y. If X in the compound of formula XXII is a leaving group Y, it is desirable for this leaving group to be less reactive than the halogen substituent T in order to avoid side reactions. To prepare compounds of formula Vb in which Z is oxygen and is attached to a —CH$_2$— group in the group R$^3$, the corresponding diol can also be employed instead of a haloalcohol of formula XXII.

Compounds of formula Vb can also be obtained by reducing acids of formula XIV to the corresponding alcohols and then converting the alcohol hydroxyl group to a leaving group Y.

Compounds of the formula VIa

Y-(CH$_2$)$_m$-R$^{2'}$ in which R$^{2'}$, m and Y have the above meanings, are known or can be prepared by known methods. For example, amine compounds of formula VIa can be obtained by reacting acids of formula XVII with amines of formula IIIb

H-R$^{2'}$ in which R$^{2'}$ has the above meaning, and then reducing the resulting amides. Amine compounds of formula VIa can also be obtained by reacting compounds of formula XII in which X denotes hydroxyl with amines of formula IIIb and converting the hydroxyl group in the resulting reaction product to a leaving group Y. Compounds of formula VIa in which R$^{2'}$ represents an OR$^4$ group can be obtained, for example, by reacting halocarboxylic acids of formula XVII with an alcohol of formula XXV

R$^4$-OH in which R$^4$ has the above meaning, and reducing the reaction product, which represents a derivative of the acid of formula XXVI R$^4$-O-(CH$_2$)$_{m-1}$-COOH in which R$^4$ and m have the above meanings, to the corresponding alcohol, and converting the hydroxyl group in the alcohol to a leaving group Y.

Compounds of formula VIb $$\overset{R^{1'}}{\underset{|}{H-N}}-(CH_2)_m-R^{2'}$$

in which R$^{1'}$, R$^{2'}$ and n have the above meanings, can be obtained by reacting compounds of formula VIa with an amine of formula XIXa in a known manner. Compounds of formula VIb in which the group R$^{2'}$ does not contain an optionally substituted benzyl group can also be obtained by hydrogenolysis of compounds of formula XXIII $$\overset{R^{1'}}{\underset{|}{B-N}}-(CH_2)_m-R^{2'''}$$

in which R$^{1'}$, m and B have the above meanings, and R$^{2'''}$ has the meaning given for R$^{2'}$ with the exception of groups containing optionally substituted benzyl groups, in particular by hydrogenolytic debenzylation of compounds of formula XXIII in which B represents benzyl. Compounds of formula XXIII can be prepared by reacting amines of formula IIIc

H-R$^{2'''}$ in which R$^{2'''}$, has the above meaning, with compounds of formula XIII'

$$\overset{R^{1'}}{\underset{|}{B-N}}-(CH_2)_m-X$$

in which R$^{1'}$, m, X and B have the above meanings.

Compounds of formula VIIa

R$^3$-O-H in which R$^3$ has the above meaning, are known. Compounds of formula VIIb

R$^3$-S-H in which R$^3$ has the above meaning, can be obtained starting from compounds of formula VIIa. For this purpose the hydroxyl group of the compounds of formula VIIa is first replaced by halogen, and the reaction product is then reacted with potassium thioacetate to give a compound of formula XXIV

R$^3$-S-CO-CH$_3$ in which R$^3$ has the above meaning. The resulting thioester is treated with an alkali metal alkoxide to obtain the alkali metal salt of the compound VIIb, which can be employed directly in further reactions.

Compounds of formula VIII can be obtained by reacting compounds of formula VIb with haloalcohols of formula XXIIa T-(CH$_2$)$_n$-OH in which T and n have the above meanings, and converting the hydroxyl group in the resulting reaction product to a leaving group Y.

Compounds of formula IX can be obtained by reacting compounds of formula IIb with an alkali metal azide or an alkali metal phthalimide in a known manner.

Compounds of formula X can be obtained by reacting compounds of formula II'

$$R^3-O-(CH_2)_n-\overset{B}{\underset{|}{N}}-(CH_2)_m-Y$$

in which R$^3$, n, m, Y and B have the above meanings, with amines of the formula IIId

H-R$^{2''}$ in which R$^{2''}$ has the above meaning. Compounds of formula II' can be obtained by reducing amides of formula XI'

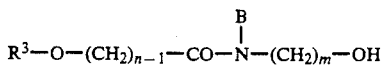

in which $R^3$, n, m and B have the above meanings, and then converting the hydroxyl group in the reaction product to a leaving group Y. Compounds of formula XI' can be obtained by reacting acids of formula XIVa $$R^3\text{-O-}(CH_2)_{n-1}\text{-COOH}$$

in which $R^3$ and n have the above meanings, with amines of formula XIII''

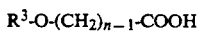

in which m and B have the above meanings.

Compounds of formula X can also be obtained by reacting compounds of formula VI''

$$Y\text{-}(CH_2)_m\text{-}R^2$$

in which $R^2$, Y and m have the above meanings, with compounds of formula XXI'

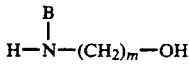

in which $R^3$, n and B have the above meanings.

Compounds of formula VI'' are known or can be prepared by known methods, for example by reacting amines of formula III with acids of formula XVII, and subsequently reducing the reaction product, or by reacting amines of formula III with compounds of formula XII in which X denotes hydroxyl, and subsequently converting the hydroxyl group to a leaving group Y.

Compounds of formula XXI can be obtained by reacting acids of formula XIVa with an amine of formula XIX'

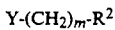

in which R¹' and B have the above meanings, and reducing the resulting amide reaction products. Compounds of formula XXI can also be obtained by reacting compounds of formula Vb'

$$R^3\text{-O-}(CH_2)_n\text{-Y}$$

in which $R^3$, n and Y have the above meanings, with compounds of formula XIX'. Compounds of formula XXI can also be obtained by reacting an alkali metal salt of a compound of formula VIIa with a compound of formula XXVII

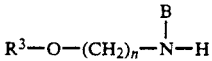

in which R¹', n, Y and B have the above meanings. Compounds of formula XXVII can be obtained by reacting a haloalcohol of formula XXIIa with an amine of formula XIX' and subsequently converting the hydroxyl group to a leaving group Y. Compounds of formula XXI' can be obtained by first reacting compounds of formula Vb, with an alkali metal azide to give the corresponding azide, and reducing the azide to the corresponding amine of formula V'

$$R^3\text{-O-}(CH_2)_n\text{-NH}_2$$

in which $R^3$ and n have the above meanings, and then reacting this amine with a benzaldehyde and reducing the Schiff base obtained as a reaction product. Amines of the formula V' in which n is 3 can also be obtained by reacting compounds of formula VIIa with acrylonitrile and reducing the reaction product.

The following examples are intended to illustrate the invention in greater detail without restricting its scope.

The stereoisomeric forms given in the examples of compounds containing a 2-(6,6-dimethylbicyclo[3.1.1-]hept-2-yl)ethyl radical can contain up to about 5% of other stereoisomeric forms of these compounds.

Example 1:
N-[2-((1R,3R,4S)-1-methyl-4-isopropylcyclohex-3yloxy)ethyl]-N-[2-mor pholin-1-yl)ethyl]-N-methylamine A) 2.1 of L-menthyloxyacetic acid (=((1R,3R,4S)1-methyl-4-isopropylcyclohex-3-yloxy)acetic acid) were dissolved in 50 ml of dichloromethane. 3.1 g of 2-chloro-1-methylpyridinium iodide, 0.8 g of N-(2-hydroxyethyl)-N-methylamine and 2.6 g of N,N-diisopropyl-N-ethylamine were added to the solution, and the reaction mixture was heated under reflux. After the reaction was completed, the reaction mixture was worked up by adding 20 ml of dilute hydrochloric acid and extracting the mixture three times with dichloromethane. The combined dichloromethane extracts were dried over sodium sulfate, filtered, and evaporated under reduced pressure. 2.6 g of crude N-(2-hydroxyethyl)-N-(methyl)-((1R,3R,4S)-1-methyl-4-isopropyl cyclohex-3-yloxy)acetamide were obtained, and were used without further purification in the next reaction step. After purification by chromatography on silica gel using n-hexane/ethanol as eluent, the product had a melting point of 65° C.–66° C.

B) 1.45 g of the product obtained above were dissolved in 10 ml of tetrahydrofuran. 0.95 g of sodium borohydride was added to the solution under a nitrogen atmosphere at a temperature of 0° C., and 1.5 g of glacial acetic acid were then added dropwise. The solution was then heated under reflux for 4 hours. The solution was worked up by evaporating the solvent under reduced pressure, adding 20 ml of water to the remaining residue, and extracting the mixture three times with 20 ml portions of dichloromethane. The combined organic phases were dried over sodium sulfate, filtered and evaporated under reduced pressure. 0.7 g of N-[2-((1R,3R,4S)-1-methyl-4-isopropylcyclo hex-3-yloxy)ethyl]-N-(2-hydroxyethyl)-N-methylamine was obtained.

C) 0.7 g of the product obtained above was dissolved in 25 ml of dichloromethane. 0.43 g of pyridine and 0.3 g of methanesulfonyl chloride were added to the solution at 0° C., and the reaction mixture was stirred at room temperature for 6 hours. The solution was then evaporated under reduced presure, and 2 ml of morpholine were immediately added to the remaining N-[2-((1R,3R,4S)-1-methyl-4-isopropylcyclohex-3-yloxy)ethyl]-N-(2-sulfonyloxy ethyl)-N-methylamine. The reaction mixture was then warmed to 40° C. for 2 hours and subsequently evaporated under reduced pressure. 10 ml of water were added to the remaining residue, and the mixture was extracted three times with 10 ml portions of ethyl acetate. The combined organic phases were dried over sodium sulfate, filtered and concentrated under reduced pressure. The crude title compound which remained was then purified by chromatography on silica gel using n-hexane/ether/ethanol as the eluent. 0.77 g of N-[2-((1R,3R,4S)-1-methyl-4-isopropylcyclohex-3-yloxy)ethyl]-N-[2-(morpholin-1-yl)ethyl]-N-methylamine was obtained.

D) N-[2-((1R,3R,4S)-1-methyl-4-isopropylcyclohex-3-yloxy)ethyl]-N-(2-morpholin-1-ylethyl)-N-methylamine base was dissolved in 2 ml of ether, and the solution was treated with saturated methanolic hydrogen chloride solution. The resulting precipitate was filtered out, washed with a little ether and dried at 40° C. 0.7 g of N-[2-((1R,3R,4S)-1-methyl-4-isopropylcyclohex-3-yloxy)ethyl]-N-[2-(morpholin-1-yl)ethyl]-N-methylamine dihydrochloride having a melting point of 218° C.-228° C. was obtained.

$[\alpha]_D^{20} = -51.1°$ (c=1; methanol)

Example 2:
N-[2-((1R,3R,4S)-1-methyl-4-isopropylcyclohex-3-yloxy)ethyl]-N-[2-(2,2-dimethylethoxy)ethyl]-N-methylamine A) 19 g of N-[2-((1R,3R,4S)-1-methyl-4-isopropylcyclohex-3-yloxy)ethyl]-N-(2-hydroxyethyl)-N-methylamine were dissolved in 200 ml of dichloromethane. 17.6 g of thionyl chloride were then added dropwise to the solution with ice-cooling. Two drops of dimethylformamide were then added as a catalyst, and the solution was heated under reflux for 3 hours. The reaction mixture was worked up by adding toluene and then evaporating the solution, after which fresh toluene was added to the residue and evaporated two more times. The remaining residue was then dissolved in dichloromethane, and ether was added dropwise to the solution to precipitate the reaction product. The resulting precipitate was filtered out and dried. 22.5 g of N-[2-((1R,3R,4S)-1-methyl-4-isopropylcyclohex-3-yloxy)ethyl]-N-(2-chloroethyl)-N-methylamine hydrochloride having a melting point of 184° C.-194° C. were obtained.

B) 2.66 g of the product obtained above were suspended in 20 ml of isobutanol. A suspension of 0.7 g of solid sodium hydroxide, which had been finely ground in a mortar, in 50 ml of isobutanol was added to the first suspension at a temperature of 0° C. The mixture was then stirred for 3 hours at a temperature of 40° C. The reaction mixture was then worked up by evaporating it under reduced pressure, adding water to the residue, and extracting the mixture with ethyl acetate. The organic phase was dried over sodium sulfate, filtered and concentrated under reduced pressure. The remaining crude product was purified by chromatography on silica gel using n-hexane/ethyl acetate/ethanol as the eluent. 2.5 g of N-[2-((1R,3R,4S)-1-methyl-4-isopropylcyclohex-3-yloxy)ethyl]-N-[2-(2,2-dimethylethoxy)ethyl]-N-methylamine were obtained.

C) 1.7 g of N-[2-((1R,3R,4S)-1-methyl-4-isopropylcyclohex-3-yloxy)ethyl]-N-[2-(2,2-dimethylethoxy)ethyl]-N-methylamine base were dissolved in 30 ml of acetone. A solution of 0.68 g of oxalic acid in 10 ml of acetone was added to the first solution. After addition of 10 ml of n-hexane, the mixture was evaporated under reduced pressure. The residue was taken up in 10 ml of 2-butanone and n-hexane was added dropwise until the mixture became turbid. 1.96 g of N-[2-((1R,3R,4S)-1-methyl-4-isopropylcyclohex-3-yloxy)ethyl]-N-[2-(2,2-dimethylethoxy)ethyl]-N-methylamine oxalate having a melting point of 113°-115° were obtained.

Example 3:
N-[2-((1R,3R,4S)-1-methyl-4-isopropylcyclohex-3-yloxy)ethyl]-N-[2-(isopropylamino)ethyl]-N-methylamine A) 5 g of N-[2-((1R,3R,4S)-1-methyl-4-isopropylcyclohex-3-yloxy)ethyl]-N-(2-chloroethyl)-N-methylamine hydrochloride were added to a mixture of 50 ml isopropanol and 50 ml water. 1.9 g of isopropylamine and 7.7 g of potassium carbonate were then added, and the reaction mixture was heated under reflux for 5 hours. The reaction mixture was worked up by diluting it with 100 ml of water and extracting the solution with ethyl acetate. The organic phase was worked up as described in Example 1 C). 4.78 g of N-[2-((1R,3R,4S)-1-methyl-4-isopropylcyclohex-3-yloxy)ethyl]-N-[2-(isopropylamino)ethyl]-N-methylamine were obtained. The free base was then converted into the corresponding hydrochloride analogously to Example 1 D). 5.1 g of N-[2-((1R,3R,4S)-1-methyl-4-isopropylcyclohex-3-yloxy)ethyl]-N-[2-(isopropylamino)ethyl]-N-methylamine dihydrochloride having a melting point of 156° C.-158° C. were obtained.

$[\alpha]_D^{20} = -55.2°$ (c=1; methanol)

Example 4:
N-[2-((1R,3R,4S)-1-methyl-4-isopropylcyclohex-3-yloxy)ethyl]-N-[3-morpholin-1-yl)propyl]-N-methylamine A) 4.2 g of L-menthyloxyacetic acid were dissolved in 50 ml of tetrahydrofuran. 2.02 g of triethylamine were added to the solution, and 2.2 g of ethyl chloroformate were added dropwise at a temperature of −10° C. 1.2 g of methylamine in a 33% strength ethanolic solution were then added, and the reaction mixture was stirred at room temperature for 2 hours. The reaction mixture was worked up by adding 100 ml of water and extracting the solution with dichloromethane. The dichloromethane extract was dried over sodium sulfate, filtered and evaporated. 3.64 g of ((1R,3R,4S)-1-methyl-4-isopropylcyclohex-3-yloxy)acetyl-N-methylamide were obtained.

B) A solution of 5.3 g of the product obtained above in 100 ml of tetrahydrofuran was added dropwise at a temperature of 0° C. under a nitrogen atmosphere to 4 g of sodium borohydride in 100 ml of tetrahydrofuran. 6 g of glacial acetic acid were then added dropwise and the reaction mixture was heated under reflux for 4 hours. The solution was worked up by evaporating it under reduced pressure. The residue was taken up in 50 ml of methanol and treated with 3 ml of concentrated hydrochloric acid. The mixture was then heated under reflux for 1 hour and subsequently evaporated to dryness (decomposition of the boron complex). The residue was taken up in 50 ml of water, and the solution was adjusted to pH 11 by addition of sodium hydroxide solution and extracted with dichloromethane. 2.9 g of crude N-[2-((1R,3R,4S)-1-methyl-4-isopropylcyclohex-3-yloxy)ethyl]-N-methylamine were obtained and used directly.

C) 6 g of the product obtained above were added to a mixture of 50 ml of isopropanol and 25 ml of water. 6 g of potassium carbonate and 3.9 g of 3-bromo-1-propanol were added to the mixture, and the reaction mixture was heated under reflux for 3 hours. The reaction mixture was worked up by distilling off the solvent under reduced pressure, adding 50 ml of water to the residue, and extracting the mixture with tert.-butyl methyl ether. The organic phase was dried over sodium sulfate, filtered and concentrated. The crude product remaining as a residue was purified by chromatography on silica gel using tetrahydrofuran/ethanol as the eluent. 5.30 g of N-[2-((1R,3R,4S)-1-methyl-4-isopropylcyclohex-3-yloxy)ethyl]-N-( 3-hydroxypropyl)-N-methylamine were obtained.

D) 5.3 g of the product obtained above were dissolved in 50 ml of dichloromethane. The solution was treated with 2 ml of thionyl chloride and 2 drops of dimethylformamide and then heated under reflux for 3 hours. The reaction mixture was then worked up analogously to Example 2 A). 5.12 g of N-[2-((1R,3R,4S)-1-methyl-4-isopropylcyclohex-3-yloxy)ethyl]-N-(3-chloropropyl)-N-methylami ne were obtained.

E) 5.0 g of the product obtained above were added to 24 ml of morpholine and the reaction mixture was stirred at 50° C. for 8 hours. The excess morpholine was then distilled off. The remaining residue was taken up in water, and the mixture was adjusted to pH 5 by adding citric acid. The aqueous phase was extracted with dichloromethane, adjusted to pH 8 by adding potassium hydrogen carbonate, and again extracted with dichloromethane. The combined dichloromethane extracts were dried over sodium sulfate and filtered, and the solvent was distilled off. 5.19 g of N-[2-((1R,3R,4S)-1-methyl-4-isopropylcyclohex-3-yloxy)ethyl]-N -[3-(morpholin-1-yl)propyl]-N-methylamine were obtained.

F) 5.19 g of N-[2-((1R,3R,4S)-1-methyl-4-isopropyl-cyclohex-3-yloxy)ethyl]-N-[3-( morpholin-1-yl)propyl]-N-methylamine were dissolved in 50 ml of dichloromethane, and the solution was treated with ethereal hydrochloric acid solution until an acidic reaction occurred. The crystalline precipitate was filtered out, washed with ether and dried at 60° C. 5.03 g of N-[2-((1R,3R,4S)-1-methyl-4-isopropylcyclohex-3-yloxy)ethyl]-N-[3-(morpholin-1-yl)propyl]-N-methylamine dihydrochloride having a melting point of 232° C.-236° C. were obtained.

$[\alpha]_D^{20} = -48.5°$ (c=1; CH$_3$OH)

Example 5:
N-[2-((1R,3R,4S)-1-methyl-4-isopropylcyclohex-3-yloxy)ethyl]-N-[2-( 3,4-dimethyoxybenzyloxy)ethyl]-N-methylamine A)4.7 g of 3,4-dimethoxybenzyl alcohol were dissolved in 50 ml of toluene. 1.1 g of a 60% strength sodium hydride dispersion were added to the solution, and the reaction mixture was heated under reflux for 1 hour. 4.4 g of N-[2-((1R,3R,4S)-1-methyl-4-isopropyl-cyc lohex-3-yloxy)ethyl]-N-(2-chloroethyl)-N-methylamine hydrochloride were then added, and the reaction mixture was heated for a further 4 hours. The reaction mixture was worked up by distilling off the solvent, adding water to the residue, and extracting the mixture with dichloromethane. The dichloromethane phase was dried over sodium sulfate and filtered, and the solvent was distilled off. 8.56 g of the crude title compound were obtained as a residue, which was purified by chromatography on silica gel using n-hexane/tetrahydrofuran as the eluent and subsequent repeated chromatography on alumina, likewise using n-hexane/tetrahydrofuran as the eluent. 4.27 g of pureN-[2-((1R,3R,4S)-1-methyl-4-isopropylcyclohex-3-yloxy)ethyl]-N-[2-(3,4-dimethox ybenzyloxy)ethyl]-N-methylamine were obtained.

B) 4.27 g of N-[2-((1R,3R,4S)-1-methyl-4-isopropyl-cyclohex-3-yloxy)ethyl]-N-[2-( 3,4-dimethoxybenzyloxy)ethyl]-N-methylamine base were dissolved in 50 ml of tetrahydrofuran. A solution of 1.22 g of fumaric acid in 15 ml of isopropanol was added to the solution. The solution was concentrated to a volume of about 20 ml under reduced pressure, and a mixture of diethyl ether/n-hexane was added until the solution became cloudy, after which the solution was cooled to 0° C. The precipitated crystals were filtered out and dried at 50° C. 4.28 g of N-[2-((1R,3R,4S)-1-methyl-4-isopropyl-cyclohex-3-yloxy)et hyl]-N-[2-(3,4-dimethoxybenzyloxy)ethyl]-N-methylamine fumarate having a melting point of 72° C.-73° C. were obtained. $[\alpha]_D^{20} = -37.0°$ (c=1; methanol)

Example 6:
N-[2-((1R,3R,4S)-1-methyl-4-isopropylcyclohex-3-yloxy)ethyl]-N-(2-eth oxyethyl)-N-methylamine A) 2.57 g of N-[2-((1R,3R,4S)-1-methyl-4-isopropyl-cyclohex-3-yloxy)ethyl]-N-(2-hyd roxyethyl)-N-methylamine were dissolved in 100 ml of tetrahydrofuran. 0.48 g of a 50% strength sodium hydride dispersion was added at room temperature, and the reaction mixture was heated under reflux for 3 hours. A solution of 1.1 g of ethyl bromide in 20 ml of tetrahydrofuran was then added dropwise to the reaction solution at boiling temperature, and the reaction solution was heated under reflux for a further 6 hours. The reaction solution was worked up by adding 2 ml of water and concentrating the mixture under reduced pressure. The remaining residue was purified by chromatography on silica gel using n-hexane/dichloromethane/methanol as the eluent. 0.55 g of oily N-[2-((1R,3R,4S)-1-methyl-4-isopropylcyclohex-3-yloxy)ethyl]-N-(2-etho xyethyl)-N-methylamine was obtained. $[\alpha]_D^{20} = -51.20°$ (c=1; methanol)

Example 7:
N-(2-[2-((1S,2S,5S)-6,6-dimethylbicyclo[3.1.1]hept-2-yl)ethylt ethyl)-N-[2-(morpholin-1-yl)ethyl]-N-methylamine A) 15.6 g of triphenylphosphine were dissolved in 300 ml of acetonitrile, and 3.02 ml of bromine were added dropwise to the solution with vigorous stirring at a temperature of 0° C. A solution of 10 g of cis-dihydronopol (=2-((1S,2S,5S)-6,6-dimethylbicyclo[3.1.1]hept-2-yl)ethanol) in 100 ml of acetonitrile was then added, and the reaction mixture was heated at 100° C. (bath temperature) for 5 hours. The reaction mixture was worked up by distilling off the solvent under reduced pressure, and the residue was purified by chromatography on silica gel using dichloromethane as the eluent. 12.0 g of 2-((1S,2S,5S)-6,6-dimethylbicyclo[3.1.1]hept-2-yl)ethyl bromide were obtained.

B) 4 g of the product obtained above were dissolved in 20 ml of dimethylformamide. 2.0 g of potassium thioacetate were added to the solution, and the reaction mixture was stirred at room temperature for 14 hours. The precipitated potassium bromide was filtered out, and the solvent was distilled off under reduced pressure. The remaining residue was purified by chromatography on silica gel using toluene/cyclohexane as the eluent.

3.8 g of 2-((1S,2S,5S)-6,6-dimethylbicyclo[3.1.1]hept-2-yl)ethyl thioacetate were obtained.

C) 2.2 g of sodium methoxide were added to a solution of 7.5 g of the product obtained above in 30 ml of methanol, and the solution was stirred at room temperature for 2 hours. The reaction mixture was then evaporated under reduced pressure. The residue containing the sodium salt of 2-((1S,2S,5S)-6,6-dimethylbicyclo[3.1.1]hept-2-yl]thioethanol was dissolved in dimethylformamide. 4.75 g of 2-bromoethanol and 9.2 g of potassium carbonate were added to the solution, and the reaction mixture was then heated under reflux for 4 hours. The reaction mixture was worked up by distilling off the solvent under reduced pressure, taking up the residue in water, and extracting with dichloromethane. The dichloromethane extract was dried over sodium sulfate, filtered and evaporated. The remaining residue was purified by chromatography on silica gel using n-hexane/ethyl acetate (7:1). 2.8 g of 2-[2-((1S,2S,5S)6,6-dimethylbicyclo[3.1.1]hept-2-yl)eth yl-thio]ethanol were obtained.

D) 2.8 g of the product obtained above were dissolved in 30 ml of dichloromethane. 1.54 g of pyridine, 2.22 g of methanesulfonyl chloride and 2 ml of triethylamine were successively added to the solution at a temperature of 0° C. The reaction mixture was stirred at room temperature for 4 hours. The mixture was worked up by extracting once by shaking with 20 ml of water, and the resulting organic phase containing the 2-[2-((1S,2S,5S)-6,6-dimethylbicyclo[3.1.1]hept-2-yl)ethylthio]ethyl methanesulfonate was dried over sodium sulfate and filtered.

E) 10 ml of N-(2-hydroxyethyl)-N-methylamine were added to the solution of 2-[2-((1S,2S,5S)-6,6-dimethylbicyclo[3.1.1]hept-2-yl)ethylthio]ethyl methanesulfonate in dichloromethane obtained above. The dichloromethane was then distilled off under reduced pressure, and the remaining reaction mixture was stirred at 60° C. for 4 hours. The reaction mixture was worked up by adding 30 ml of water and extracting the mixture with ethyl acetate. The organic phase was separated and concentrated. The remaining residue was purified by chromatography on silica gel using n-hexane/dichloromethane/methanol as the eluent. 2.6 g of N-(2-[2((1S,2S,5S)-6,6-dimethylbicyclo[3.1.1]hept-2-yl)ethylthio]ethyl]-N-(2-hydroxyethyl)-N-methylamine were obtained.

F) 2.6 g of the product obtained above were dissolved in 100 ml of dichloromethane and 1.52 g of pyridine, and 1.6 g of methanesulfonyl chloride were then added to the solution at a temperature of 0° C. The solution was then stirred at room temperature for 15 hours. The reaction mixture was then concentrated to dryness under reduced pressure. The crude N-(2-[2-((1S,2S,5S)-6,6-dimethylbicyclo[3.1.1]hept-2-yl)ethylthio]ethyl)-N-(2 -sulfonyloxyethyl)-N-methylamine remaining as a residue was used without further purification. G) 10 ml of morpholine were added to the product obtained above, and the reaction mixture was stirred at 60° C. for 6 hours. The solution was worked up by concentrating it under reduced pressure, taking up the residue in water and extracting with ethyl acetate. The extract was purified by chromatography on silica gel using ethyl acetate/dichloromethane as the eluent. 2.8 g of N-(2-[2((1S,2S,5S)-6,6-dimethylbicyclo[3.1.1]hept-2-yl)ethylthio]ethyl)-N-[2-(morpholin-1-yl)ethyl]-N-methylamine were obtained.

H) 2.8 g of the free base obtained above were dissolved in 20 ml of methanol. The solution was treated with methanolic hydrochloric acid solution until an acidic reaction occurred. The solution was then evaporated under reduced pressure, and the residue was recrystallized from methanol/diethyl ether. 2.7 g of N-(2-[2-((1S,2S,5S)-6,6-dimethylbicyclo[3.1.1]hept-2 -yl)ethylthio]ethyl)-N-[2-(morpholin-1-yl)ethyl]-N-methylamine dihydrochloride having a melting point of 189° C.-209° C. were obtained.

$[\alpha]_D^{20} = -15.1°$ (c=1; methanol)

Example 8:

N-[2-((1R,3R,4S)-1-methyl-4-isopropylcyclohex-3yloxy)ethyl]-N-(2-dieth ylaminoethyl)-N-ethylamine A) 5.0 g of ((1R,3R,4S)-1-methyl-4-isopropylcyclohex-3-yloxy)acetic acid were dissolved in 100 ml of tetrahydrofuran. 3.4 g (=4.2 ml) of N,N,N'-triethylethylenediamine and 5.3 g of dicyclohexylcarbodiimide were added to the solution, and the reaction mixture was stirred at room temperature for 24 hours. The mixture was worked up by concentrating it under reduced pressure. The remaining residue was purified by chromatography on silica gel using dichloromethane/methanol as the eluent. 4.8 g of N-(2- diethylaminoethyl)-N-(ethyl)-((1R,3R,4S)-1-methyl-4-isopropylcyclohex-3-yloxy)acetamide were obtained.

B) 1.4 g of the product obtained above were dissolved in 20 ml of tetrahydrofuran. The solution was added dropwise under a nitrogen atmosphere to a suspension of 0.3 g of lithium aluminium hydride in 20 ml of tetrahydrofuran, and the reaction mixture was then heated under reflux for 6 hours. To work up the reaction mixture, it was cooled to 0° C., and 1 ml of water and 4 ml of an aqueous 1N sodium hydroxide solution were added dropwise. The resulting precipitate was filtered out, and the filtrate was concentrated under reduced pressure. 20 ml of water were added to the residue, and the latter was extracted with dichloromethane. After concentration of the dichloromethane extract, 0.82 g of N-[2-((1R,3R,4S)-1-methyl-4-isopropylcyclohex-3-yloxy)ethyl]-N-(2-diethylaminoethyl)-N-ethylamine was obtained.

C) 0.82 g of the base obtained above were dissolved in 10 ml of acetone, and a solution of 0.62 g of oxalic acid dihydrate in 5 ml of acetone was added. The mixture was cooled in a refrigerator for 24 hours, and the resulting precipitate was filtered out. 0.45 g of N-[2((1R,3R,4S)-1-methyl-4-isopropylcyclohex-3-yloxy) ethyl]-N-(2-diethylaminoethyl)-N-ethylamine dioxalate having a melting point of 103° C.-108° C. was obtained.

$[\alpha]_D^{20} = -39.1°$ (c=1; methanol)

Example 9:

N-[2-((1R,3R,4S)-1-methyl-4-isopropylcyclohex-3-yloxy)ethyl]-N-(2-(mor pholin-1-yl)ethyl]-N-methylamine A) 33 g of N-benzyl-N-methyl-2-aminoethanol were dissolved in 300 ml of dichloromethane. 48 g of thionyl chloride and 2 drops of dimethylformamide were added to the solution at 0° C. The reaction mixture was then heated under reflux for 6 hours. The reaction mixture was worked up by evaporating it to dryness and taking up the residue three times in 300 ml portions of toluene and again evaporating to dryness. The remaining residue was dissolved in dichloromethane and the N-benzyl-N-(2-chloroethyl)-N-methylamine hydrochloride was crystallized by addition of diethyl ether to the solution. The crystals (m.p. 142° C.–145° C.) were filtered out and dissolved in ice water. The solution was adjusted to alkaline pH 9 by addition of aqueous sodium hydroxide solution and then extracted with toluene. The organic phase was separated, dried over sodium sulfate, filtered and concentrated under reduced pressure. 29 g of N-benzyl-N-(2- chloroethyl)-N-methylamine were obtained as a residue.

B) 23 g of L-menthol were dissolved in 200 ml of toluene. A suspension of 9 g of sodium hydride in 200 ml of toluene was added to the solution under a nitrogen atmosphere at a temperature of 0° C. The reaction mixture was then heated under reflux for 3 hours. A solution of 29 g of the product obtained above under A) in 100 ml of toluene was then added, and the reaction mixture was heated under reflux for a further 4 hours. To work up the mixture, it was cooled to a temperature of 0° C., and 20 ml of methanol were added dropwise. 300 ml of ice water and 200 ml of dilute aqueous hydrochloric acid solution were then added, and the mixture was extracted with ethyl acetate. The organic phase was discarded, and the aqueous phase was rendered alkaline (pH 10) by addition of aqueous sodium hydroxide solution. Sodium chloride was then added, and the mixture was again extracted with ethyl acetate. The ethyl acetate phase was dried over sodium sulfate, filtered and concentrated under reduced pressure. 44 g of crude N-[2-((1R,3R,4S)-1-methyl-4-isopropylcyclohex-3-yloxy)ethyl ]-N-benzyl-N-methylamine were obtained and directly reacted further.

C) 44 g of the product obtained above were dissolved in 200 ml of ethanol, and concentrated aqueous hydrochloric acid was added to the solution until an acidic reaction occurred. 20 g of hydrogenation catalyst (palladium/carbon 10% strength) were added to the solution, and the reaction mixture was hydrogenated at room temperature and a hydrogen pressure of 5 bar. After hydrogenation was complete, the catalyst was filtered out, and the solution was concentrated under reduced pressure. 29.2 g of crude N-[2-((1R,3R,4S)-1-methyl-4-isopropylcyclohex-3-yloxy )ethyl]-N-methylamine were obtained.

D) 29.2 g of the product obtained above were dissolved in a mixture of 300 ml isopropanol and 200 ml water. 36.5 g of N-(2-chloroethyl)morpholine hydrochloride and 50 g of potassium carbonate were then added to the mixture, and the reaction mixture was heated under reflux for 6 hours. The reaction mixture was worked up by concentrating it to one-half volume under reduced pressure and then extracting it with ethyl acetate. The ethyl acetate extract was worked up as described in Example 1 C). 20.8 g of N-[2-((1R,3R,4S)-1-methyl-4-isopropylcyclohex-3-yloxy)ethyl]-N-[2-(morpholin-1-yl)ethyl]-N-methylamine dihydrochloride having a melting point of 218° C.–228° C. were obtained.

Example 10:
N-(5-[2-((1S,2S,5S)-6,6-dimethylbicyclo[3.1.1]hept-2-yl)ethoxy]-p entyl)-N-[2-morpholin-1-yl)ethyl]-N-methylamine.

A) 200 g of cis-dihydronopol were dissolved in 340 ml of toluene. 200 ml of thionyl chloride were added dropwise to the solution. 5 ml of dimethylformamide were then added, and the reaction mixture was heated under reflux for 4 hours. The reaction mixture was worked up by distilling off the solvent under reduced pressure, taking up the residue in 300 ml of toluene, concentrating the solution to dryness, taking up the residue again in 300 ml of toluene, and evaporating the solution again to dryness. 206 g of crude 2-((1S,2S,5S)-6,6-dimethylbicyclo[3.1.1]hept-2-yl)ethyl chloride were obtained and used in the next step without further purification.

B) Over the course of 12 hours, 12.2 g of elemental sodium were dissolved in portions in 357 ml of 1,5-pentanediol at a temperature of 90° C. 80 g of 2-((1S,2S,5S)-6,6-dimethylbicyclo[3.1.1]hept-2-y l)ethyl chloride were then added dropwise to this solution, and the reaction mixture was heated at 130° C. for 15 hours. The reaction mixture was worked up by cooling to room temperature, adding 300 ml of a 5% strength aqueous hydrochloric acid solution, and extracting the mixture with ether. After concentrating the ether extract, 99.6 g of crude 5-[2-((1S,2S,5S)-6,6-dimethylbicyclo[3.1.1-]hept-2-yl )ethoxy]pentanol were obtained.

C) 99.6 g of the product obtained above were dissolved in 120 ml of toluene. 1 ml of dimethylformamide was added to the solution, and 65 ml of thionyl chloride were then added dropwise at room temperature and the reaction mixture was heated under reflux for 3 hours. The reaction mixture was worked up as described in Example 10 A). 102.1 g of crude 5-[2-((1S,2S,5S)-6,6-dimethylbicyclo[3.1.1]hept-2-yl)ethoxy]pentyl chloride were obtained and used directly in the next reaction step.

D) 10 g of potassium carbonate and 3.33 g of N-benzyl-N-methylamine were added to a solution of 7.2 g of the product obtained above in 80 ml of isopropanol and 20 ml of water. The solution was heated under reflux for 30 hours. The solvent was distilled off under reduced pressure. 30 ml of water were added to the remaining residue, and the aqueous mixture was then extracted with dichloromethane. The dichloromethane extract was concentrated and purified by chromatography on silica gel using dichloromethane as the eluent. 5.7 g of N-(5-[2-((1S,2S,5S)-6,6dimethylbicyclo[3.1.1]hept-2-yl)ethoxy]pe ntyl)-N-benzyl-N-methylamine were obtained.

E) 5.7 g of the product obtained above were dissolved in a mixture of 80 ml of ethanol and 20 ml of water. 20 ml of concentrated hydrochloric acid and 10 g of palladium/carbon catalyst (10% strength) were added to the solution, and the reaction mixture was hydrogenated at room temperature and a hydrogen pressure of 3 bar. After hydrogenation was complete, the catalyst was filtered out and the solution was concentrated under reduced pressure. 30 ml of water were added to the residue, and the mixture was acidified with hydrochloric acid and extracted with dichloromethane. After evaporation of the dichloromethane extract, 2.03 g of N-(5-[2-((1S,2S,5S)-6,6-dimethylbicyclo[3.1.1]hept-2-yl)ethoxy]pentyl)-N-methylamine hydrochloride were obtained.

F) 2.03 g of the product obtained above were dissolved in a mixture of 80 ml of isopropanol and 20 ml of water. 8 g of potassium carbonate and 1.5 g of N-(2-chloroethyl)morpholine hydrochloride were added successively to the solution, and the reaction mixture was stirred at 80° C. for 3 hours. The reaction mixture was worked up by evaporating the solvent under reduced pressure. 20 ml of water were added to the residue, and the mixture was extracted with dichloromethane. The residue which remained after concentration of the dichloromethane extract was purified by chromatography on silica gel using toluene/ethanol/ammonia (80:20:1). 1.57 g of N-(5-[2-((1S,2S,5S)-6,6-dimethylbicyclo[3.1.1]hept-2-yl) ethoxy]pentyl)-N-[2-(morpholin-1-yl)ethyl]-N-methylamine were obtained.

G) The amine obtained above was dissolved in 30 ml of dichloromethane. Ethereal hydrochloric acid was added to the solution until an acidic reaction occurred. The solution was concentrated in vacuo, and the residue was recrystallized from isopropanol. 0.7 g of N-(5-[2-(1S,2S,5S)-6,6-dimethylbicyclo[3.1.1]he pt-2-yl)ethoxy]pentyl)-N-[2-(morpholin-1-yl)ethyl]-N-methylamine dihydrochloride having a melting point of 228° C.–240° C. was obtained.

Example 11:
N-(5-[2-((1S,2S,5S)-6,6-dimethylbicyclo[3.1.1]hept-2-yl)ethoxy]pe
ntyl)-N-[2,2-dimethylethoxy)ethyl]-N-methylamine 15 g of 5-[2-((1S,2S,5S)-6,6-dimethylbicyclo[3.1.1-]hept-2-yl)ethoxy]pentyl chloride were dissolved in 100 ml of dimethylformamide. 5.13 g of N-[2-(2,2-dimethylethoxy)ethyl]-N-methylamine (Example 12 B)), 12 g of potassium carbonate and 1 g of potassium iodide were added to the solution. The reaction mixture was stirred at a temperature of 80° C. for 12 hours. The reaction mixture was worked up by concentrating it under reduced pressure, adding 100 ml of water to the residue, and extracting the mixture three times with 80 ml portions of dichloromethane. The combined dichloromethane extracts were dried over sodium sulfate, filtered and concentrated. The crude product remaining as a residue was purified by chromatography on silica gel using dichloromethane/methanol as the eluent. 4.1 g of oily N-(5-[2-((1S,2S,5S)-6,6-dimethylbicyclo[3.1.1-]hept-2-yl)ethoxy]pent yl)-N-[2-(2,2-dimethylethoxy)ethyl]-N-methylamine were obtained.

$[\alpha]_D^{20} = -9.1°$ (c=1; water)

Example 12:
N-(2-[2-((1S,2S,5S)-6,6-dimethylbicyclo[3.1.1]hept-2-yl)ethoxy]et
hyl)-N-[2-(2,2-dimethylethoxy)ethyl]-N-methylamine A) A solution of 5.0 g of isobutanol in 50 ml of toluene was added at a temperature of 0° C. to a solution of 3.25 g of sodium hydride in 100 ml of toluene, and the reaction mixture was heated under reflux for 3 hours. 12.4 g of N-benzyl-N-methyl-2-chloroethylamine were then added to the reaction mixture, and the solution was heated under reflux for a further 8 hours. The reaction solution was worked up by cautiously adding 5 ml of methanol and then 100 ml of water, and the pH was then adjusted to pH 2 by adding dilute aqueous hydrochloric acid solution. After shaking, the organic phase was separated and discarded. The aqueous phase was adjusted to pH 13 by addition of aqueous sodium hydroxide solution and extracted with ethyl acetate. The ethyl acetate extract was dried over sodium sulfate, filtered and concentrated. The remaining residue was purified by chromatography on silica gel using n-hexane/ethyl acetate as the eluent. 10.7 g of N-[2-(2,2-dimethylethoxy)ethyl]-N-benzyl-N-methylamine were obtained.

B) 8.9 g of the product obtained above were dissolved in 200 ml of ethanol. 6 g of palladium/carbon hydrogenation catalyst (5% strength) and 5.2 ml of concentrated aqueous hydrochloric acid were added to the solution. The mixture was then hydrogenated at room temperature under a hydrogen pressure of 3.5 bar. After hydrogenation was complete, the catalyst was filtered out, the filtrate concentrated under reduced pressure, and the remaining residue was purified by chromatography on silica gel using dichloromethane/methanol as the eluent. 5.13 g of N-[2-(2,2-dimethylethoxy)ethyl]-N-methylamine were obtained.

C) 5.13 g of the product obtained above were dissolved in 30 ml of dimethylformamide. 12 g of potassium carbonate and 10.7 g of 2-bromoethanol were added to the solution and the reaction mixture was then stirred at a temperature of 60° C. for 12 hours. The reaction mixture was worked up by adding 200 ml water and extracting with ethyl acetate. The ethyl acetate extract was dried over sodium sulfate, filtered and concentrated. After chromatographic purification of the remaining residue, 3.9 g of N-(2-(2,2-dimethylethoxy)ethyl)-N-(2-hydroxyethyl)-N-methylamine were obtained.

D) 3.9 g of the product obtained above were dissolved in 50 ml of dichloromethane. 5.3 g of thionyl chloride and 2 drops of dimethylformamide were added to the solution. The reaction mixture was heated under reflux for 5 hours. The mixture was worked up by concentrating to dryness, taking up the residue using 100 ml portions of toluene and evaporating the solution to dryness again two times. The residue which remained was dissolved in a little dichloromethane, and n-hexane was added dropwise to the solution until it became cloudy. The mixture was then stored in a refrigerator for 12 hours, and the precipitated crystals were filtered out and dried. 3.77 g of N-[2-(2,2-dimethylethoxy)ethyl]-N-(2-chloroethyl)-N-methylamine hydrochloride were obtained.

E) 3.3 g of the product obtained above were dissolved in 20 ml of cis-dihydronopol. 1.6 g of solid sodium hydroxide, which had been finely ground in a mortar, were added to the solution at a temperature of 0° C. The reaction mixture was then stirred at a temperature of 40° C. for 7 hours. The reaction mixture was worked up by concentrating it under reduced pressure, adding 50 ml of water to the residue, and extracting the mixture with ethyl acetate. The residue remaining after concentration of the extract was purified by chromatography on silica gel using dichloromethane/methanol as the eluent. 1.6 g of N-(2-[2-((1S,2S,5S)-6,6-dimethylbicyclo[3.1.1]hept-2-yl)eth oxy]ethyl-N-[2-(2,2-dimethylethoxy)ethyl]-N-methyl-amine were obtained.

F) 1.6 g of the product obtained above were dissolved in 20 ml of dichloromethane, and methanolic hydrochloric acid was added to the solution until an acidic reaction occurred. The solution was then evaporated under reduced pressure. The residue was dissolved in 50 ml of toluene, the solution was concentrated again under reduced pressure, and the residue was dissolved in 5 ml of dichloromethane. n-Hexane was added to the solution until the appearance of turbidity. The mixture was then allowed to stand overnight in the refrigerator. The crystals which precipitated were then filtered out and dried. 1.2 g of N-(2-[2-((1S,2S,5S)-6,6-dimethylbicyclo[3.1.1]hept-2 -yl)ethoxy]ethyl-N-[2-(2,2-dimethylethoxy)ethyl]-N-methylamine hydrochloride having a melting point of 86° C.–88° C. were obtained.

Example 13:
N-[2-((1R,3R,4S)-1-methyl-4-isopropylcyclohex-3-yloxy)ethyl]-N-(2-aminoethyl)-N-methylamine A) 4.5 g of N-[2-((1R,3R,4S)-1-methyl-4-isopropylcyclohex-3-yloxy)ethyl]-N-(2-chlo roethyl)-N-methylamine were added to a mixture of 40 ml water and 20 ml tetrahydrofuran. 2 g of potassium carbonate and 1 g of sodium azide were added to the mixture. The reaction solution was then stirred at room temperature for 8 hours. The reaction solution was worked up by concentrating to about 30 ml and extracting the aqueous phase with ethyl acetate. After concentration of the ethyl acetate extract, 4.5 g of crude N-[2-((1R,3R,4S)-1-methyl-4-isopropylcyclohex-3-ylo xy)ethyl]-N-(2-azidoethyl)-N-methylamine were obtained, which was used in the next step without further purification.

B) 4.5 g of the crude product obtained above were dissolved in 200 ml of ethanol. 3 g of palladium/carbon hydrogenation catalyst (10% strength) were added to the solution, and the reaction mixture was hydrogenated at room temperature and a hydrogen pressure of 5 bar. The reaction mixture was worked up by filtering out the catalyst and concentrating the filtered solution to dryness under reduced pressure. The crude title compound which remained was dissolved in tetrahydrofuran and purified on magnesium silicate. 3.95 g of N-[2-((1R,3R,4S)-1-methyl-4-isopropylcyclohex-3-yloxy)ethyl]-N-(2-aminoethyl)-N-methylamine were obtained.

C) 1.42 g of the base obtained above were dissolved in 40 ml of tetrahydrofuran and 5 ml of methanol. 1.29 g of fumaric acid were added to the solution, and the reaction mixture was stirred at room temperature for 8 hours. The precipitated crystals of the fumarate of the title compound were filtered out and dried under reduced pressure. 1.50 g of N-[2-((1R,3R,4S)-1-methyl-4-isopropylcyclohex-3-yloxy)ethyl]-N-(2-aminoethyl)-N-methylam ine difumarate having a melting point of 152° C.-154° C. were obtained.

Example 14:
N-[3-((1R,3R,4S)-1-methyl-4-isopropylcyclohex-3-yloxy)propyl]-N-[2-(morpholin-1-yl)ethyl]amine A) 1 g of a sodium hydride suspension (50% strength) in paraffin oil was added at a temperature of 0° C. to a solution of 30 g of L-menthol in 300 ml of dichloromethane. A solution of 12.5 ml acrylonitrile in 50 ml dichloromethane was slowly added dropwise, and the reaction mixture was then stirred at room temperature for a further 5 hours. The reaction mixture was worked up by cautiously adding 10 ml of glacial acetic acid, followed by 200 ml of water, and then extracting the mixture with dichloromethane. The dichloromethane extract was dried over sodium sulfate, filtered and concentrated. After chromatographic purification of the residue on silica gel using n-hexane/dichloromethane as the eluent, 25.03 g of crude 2-((1R,3R,4S)-1-methyl-4-isopropylcyclohex-3-yloxy)propionitrile were obtained and used for the next reaction step without further purification.

B) 25 g of the product obtained above were dissolved in 100 ml of methanol. 50 ml of concentrated aqueous ammonia solution were added to the solution. 20 g of Raney nickel were then added, and the reaction mixture was hydrogenated at room temperature and a hydrogen pressure of 4 bar. After the absorption of hydrogen was completed, the catalyst was filtered out, and the filtrate was evaporated under reduced pressure. 200 ml of water were added to the residue, and the mixture was extracted with tert.-butyl methyl ether. The organic phase was concentrated, and the residue was chromatographed on silica gel using dichloromethane/methanol/ammonia as the eluent. 22.33 g of 3-((1R,3R,4S)-1-methyl-4-isopropylcyclohex-3-yloxy)propylamine were obtained.

C) 19.98 g of the product obtained above were dissolved in 200 ml of ethanol. 10.5 ml of benzaldehyde were added to the solution, and the reaction mixture was warmed to 50° C. for 1 hour. It was then cooled to 0° C.; 3.6 g of sodium borohydride were added in portions, and the reaction mixture was allowed to react for a further hour. The reaction mixture was worked up by cautiously adding 10 ml of water and adjusting the mixture to pH 10 by adding 2N aqueous hydrochloric acid. The ethanol was distilled off, and the remaining aqueous phase was extracted with diethyl ether. After evaporation of the ether extract, 28.3 g of crude N-[3-((1R,3R,4S)-1-methyl-4-isopropylcycloh ex-3-yloxy)-propyl]-N-benzylamine were obtained.

D) 9.65 g of the product obtained above were dissolved in a mixture of 50 ml isopropanol and 30 ml water. 10.0 g of N-(2-chloroethyl)morpholine hydrochloride and 9.0 g of potassium carbonate were then added to the solution, and the reaction mixture was heated under reflux for 10 hours. The reaction mixture was worked up by distilling the isopropanol off from the reaction mixture under reduced pressure, and the aqueous phase was extracted with dichloromethane. The dichloromethane phase was dried over sodium sulfate, filtered and concentrated. After chromatographic purification of the remaining residue on silica gel using n-hexane/tetrahydrofuran as the eluent, 9.89 g of N-[3-((1R,3R,4S)-1-methyl-4-isopropylcyclohex-3-yloxy)propyl]-N-[2-(morpholin-1-yl)ethyl]-N-benzylamine were obtained.

E) 5.5 g of the product obtained above were dissolved in a mixture of 100 ml ethanol and 20 ml water. 12 ml of aqueous 2N hydrochloric acid and 10 g of palladium/carbon hydrogenation catalyst (10% strength) were added to the solution, and the reaction mixture was hydrogenated at room temperature under a hydrogen pressure of 4.5 bar. After the absorption of hydrogen was completed, the catalyst was filtered out, and the filtered solution was evaporated in vacuo. Dilute aqueous sodium hydroxide (pH 11) was added to the residue, and the mixture was extracted with tert.-butyl methyl ether. The organic phase was dried over sodium sulfate, filtered and concentrated. 4.03 g of N-[3-((1R,3R,4S)-1-methyl-4-isopropylcyclohex-3-yloxy)-propyl]-N-[2-(morpholin-1-yl)ethyl]amine were obtained. The free base was converted into N-[3-((1R,3R,4S)-1-methyl-4-isopropylcyclohex-3-yloxy)-propyl]-N-[2-(mo rpholin-1-yl)ethyl]amine dihydrochloride having a melting point of 222° C.-226° C. analogously to the method described in Example 1D.

Example 15:
N-[3-((1R,3R,4S)-1-methyl-4-isopropylcyclohex-3-yloxy)propyl-N-[2-(mo rpholin-1-yl)ethyl]-N-methylamine A) 4 g of N-[3-((1R,3R,4S)-1-methyl-4-isopropylcyclohex-3-yloxy)propyl]-N-[2-(mo rpholin-1-yl)ethyl]amine were dissolved in 100 ml of ethanol. 1.4 ml of 37% strength formaldehyde solution and about 5 g of palladium/carbon hydrogenation catalyst (10% strength) were added to the solution, and the reaction mixture was hydrogenated at room temperature under a hydrogen pressure of 4.5 bar. After the absorption of hydrogen was completed, the catalyst was filtered out, and the filtrate was evaporated under reduced pressure. The residue was taken up in 20 ml of water, and the solution was extracted with ether. After evaporation of the ether extract, 3.85 g of N-[3-((1R,3R,4S)-1-methyl-4-isopropylcyclohex-3-yloxy)propyl]-N-[2-(morpholin-1-yl)ethyl]-N-methylamine were obtained.

B) 3.85 g of the free base obtained above were dissolved in 60 ml of dichloromethane. An ethereal hydrochloric acid solution was added to the solution until an acidic reaction occurred. The precipitated crystals were filtered out and washed with 50 ml of a 1:1 mixture of diethyl ether/n-hexane and then recrystallized from a mixture of 2-butanone/ethanol (up to 10%). 3.90 g of N-[3-(1R,3R,4S)-1-methyl-4-isopropylcyclohex-3-yloxy)propyl]-N -[2-morpholin-1-yl)ethyl]-N-methylamine dihydrochloride having a melting point of 193° C.–196° C. were obtained.

Example 16:
N-[2-((1R,3R,4S)-1-methyl-4-isopropylcyclohex-3-yloxy)ethyl]-N-[2-( 2,2-dimethylethoxy)ethyl]amine A) 49.4 g of 2-chloro-1-methylpyridinium iodide were added to a solution of 34.3 g of ((1R,3R,4S)-1-methyl-4-isopropylcyclohex-3-yloxy)acetic acid in 350 ml of dichloromethane, and the reaction mixture was stirred at room temperature for 1 hour. 24.2 g of 2-(benzylamino)ethanol and 41.4 g of N,N-diisopropyl-N-ethylamine were then added dropwise at a temperature of 0° C. The solution was then heated under reflux for 6 hours. The reaction mixture was worked up by extracting once by shaking with aqueous 1N hydrochloric acid and once by shaking with aqueous sodium hydroxide. The organic phase was then dried over sodium sulfate, filtered and concentrated under reduced pressure. 57.6 g of crude N-(2-hydroxyethyl)-N-(benzyl)-((1R,3R,4S)-1-methyl -4-isopropylcyclohix-3-yloxy)acetamide were obtained.

B) A solution of 20 g of the product obtained above in 200 ml of tetrahydrofuran were added at room temperature under a nitrogen atmosphere to 11.4 g of sodium borohydride contained in 200 ml of tetrahydrofuran. 18 ml of acetic acid were then added dropwise over a period of 30 minutes, and the mixture was heated under reflux for 6 hours. The solution was worked up by concentrating it under reduced pressure and cautiously adding 200 ml of water to the remaining residue. The mixture was then adjusted to pH 10 by addition of aqueous 2N sodium hydroxide solution and extracted with dichloromethane. After concentration of the dichloromethane extract, 18.4 g of crude N-[2-((1R,3R,4S)-1-methyl-4-isopropylcyclohex-3-ylox y)ethyl]-N-(2-hydroxyethyl)-N-benzylamine were obtained and used without further purification for the next reaction step.

C) A solution of 8 g of the product obtained above in 70 ml of dichloromethane was added dropwise to a solution of 8 g of thionyl chloride in 100 ml of dichloromethane. Two drops of dimethylformamide were then added as a catalyst, and the solution was heated under reflux for 4 hours. The solution was worked up by evaporating the solvent and taking up the residue using 100 ml portions of toluene and evaporating to dryness again three times. The remaining residue was dissolved in 50 ml of dichloromethane, and diethyl ether was added dropwise to the solution until it became turbid. The mixture was allowed to stand in a refrigerator for 12 hours. The precipitated crystals were then filtered out and dried under reduced pressure 6.7 g of N-[2-((1R,3R,4S)-1-methyl-4-isopropylcyclohex-3-yloxy)ethyl]-N-(2-chloroethyl)-N-benzyla mine hydrochloride were obtained.

D) 6.7 g of the product obtained above were dissolved in 150 ml of isobutanol. 1.6 g of solid sodium hydroxide which had been finely ground in a mortar were added to the solution at a temperature of 0° C., and the mixture was then stirred at 40° C. for 6 hours. The solution was worked up by evaporating it under reduced pressure, taking up the remaining residue in 100 ml of water, and extracting the solution with ethyl acetate. After distilling off the ethyl acetate from the extract, 6.55 g of crude product were obtained as a residue. This was purified by chromatography on silica gel using n-hexane/dichloromethane as the eluent. 6.03 g of N-[2-((1R,3R,4S)-1-methyl-4-isopropylcyclohex-3-yloxy)ethyl]-N-[2-(2,2 -dimethylethoxy)ethyl]-N-benzylamine were obtained.

E) 3 g of the product obtained above were dissolved in a mixture of 100 ml of ethanol and 30 ml of water. 1.5 g of concentrated hydrochloric acid and 2.5 g of palladium/carbon hydrogenation catalyst (5% strength) were successively added to the solution, and the mixture was hydrogenated at room temperature under a hydrogen pressure of 4 bar. The absorption of hydrogen was complete after about 3 hours. The catalyst was filtered out, and the filtrate was evaporated under reduced pressure. The remaining residue was taken up in 100 ml of water and extracted with ethyl acetate. The organic phase was dried over sodium sulfate, filtered and concentrated under reduced pressure. The crude title compound obtained was purified by chromatography on silica gel using n-hexane/dichloromethane as the eluent. 1.8 g of oily N-[2-((1R,3R,4S)-1-methyl-4-isopropylcyclohex-3-yloxy)ethyl]-N-(2,2-dim ethylethoxy)ethyl]amine were obtained. $[\alpha]_D^{20} = -58.2°$ (c=1; methanol)

Example 17:
N-[2-((1R,3R,4S)-1-methyl-4-isopropylcyclohex-3-yloxy)ethyl]-N-[2-( 4-phenylbutylamino)ethyl]-N-methylamine A) 3.07 g of N-[2-((1R,3R,4S)-1-methyl-4-isopropylcyclohex-3-yloxy)ethyl]-N-(2-chl oroethyl)-N-methylamine hydrochloride were mixed with 8.8 g of 4-phenylbutylamine. The reaction mixture was stirred at a temperature of 45° C. for 8 hours. The reaction mixture was purified and simultaneously freed of excess 4-phenylbutylamine by chromatography on silica gel using tert.-butyl methyl ether. 3.52 g of oily N-[2-((1R,3R,4S)-1-methyl-4-isopropylcyclohex-3-yloxy)ethyl]-N-[2-( 4-phenylbutylamino)ethyl]-N-methylamine were obtained.

B) 3.5 g of the oily title base obtained above were dissolved in 20 ml of tetrahydrofuran. A solution of 2.1 g of fumaric acid in 50 ml of tetrahydrofuran was added to the solution. Diethyl ether was then added to the reaction mixture until it became turbid, and the mixture was stored in a refrigerator for 12 hours. The precipitated crystals were filtered out and dried. 4.4 g of the difumarate of the title compound having a melting point of 156° C.–158° C. were obtained. $[\alpha]_D^{20} = -30.7°$ (c=1; CH$_3$OH)

Example 18:
N-[2-((1R,3R,4S)-1-methyl-4-isopropylcyclohex-3-yloxy)ethyl]-N-[2-( 3,4,5-trimethoxybenzylamino)ethyl]-N-methylamine A) 6.5 g of N-[2-((1R,3R,4S)-1-methyl-4-isopropylcyclohex-3-yloxy)ethyl]-N-(2-chlo roethyl)-N-methylaminehydrocholride were added to 15 ml of isopropanol. 25 ml of 3,4,5-trimethoxybenzylamine were then added, and the reaction mixture was stirred at a temperature of 40° C. for 8 hours. The reaction mixture was worked up by distilling off the solvent and dissolving the residue in 150 ml of tert.-butyl methyl ether. To remove excess 3,4,5-trimethoxybenzylamine, dilute aqueous hydrochloric acid was added to the solution (pH of the aqueous phase=7). The organic phase was separated, dried over sodium sulfate, filtered and concentrated under reduced pressure. The crude product which remained as a residue was purified by chromatography on silica gel using n-hexane to which amounts of tetrahydrofuran increasing from 30 to 100% were added. 8.2 g of oily N-[2-((1R,3R,4S)-1-methyl-4-isopropylcyclohex-3-yloxy)ethyl]-N-[2-(3,4,5-trimethoxybenzylamino)ethyl]-N-methylamine were obtained.

B) 1.7 g of the oily title base obtained above were dissolved in 10 ml of tetrahydrofuran. A solution of 0.95 g of fumaric acid in 10 ml of tetrahydrofuran was added to the solution. The reaction mixture was concentrated under reduced pressure, 20 ml of isopropanol were then added, and the mixture was stirred at 50° C. for 5 hours. It was then cooled to room temperature, and the precipitated crystals were filtered out. 1.50 g of the difumarate of the title compound having a melting point of 127° C. to 134° C. were obtained.

Example 19:
N-[2-((1R,3R,4S)-1-methyl-4-isopropylcyclohex-3-yloxy)ethyl]-N-(2-[N'-(3,4,5-trimethoxybenzyl)-N'-methylamino]ethyl)-N-methylamine A) 4.1 g of N-[2-((1R,3R,4S)-1-methyl-4-isopropylcyclohex-3-yloxy)ethyl-N-[2-(3 ,4,5-trimethoxybenzylamino)ethyl]-N-methylamine were dissolved in 100 ml of methanol. 2.5 ml of 37% strength formaldehyde solution and about 3 g of Raney nickel were added to the solution. The reaction mixture was then hydrogenated at a hydrogen pressure of 4.5 bar for 8 hours. The reaction mixture was worked up by filtering out the catalyst, and concentrating the filtrate under reduced pressure. The residue was taken up in dichloromethane and extracted twice with water. The aqueous phase was extracted twice more with dichloromethane. The combined organic phases were then dried over sodium sulfate, filtered and concentrated under reduced pressure 3.65 g of N-[2((1R,3R,4S)-1-methyl-4-isopropylcyclohex-3-yloxy)ethyl]-N-[2-[N'-(3,4,5-trimethoxybenzyl)-N'-methlamino]ethyl)-N-methylamine were obtained.

B) The title base was dissolved in 20 ml of tetrahydrofuran. A solution of 1.8 g of fumaric acid in 20 ml of tetrahydrofuran was added to the solution Diethyl ether was added to the solution it became turbid, and the reaction mixture was allowed to stand in a refrigerator for 12 hours. The precipitated crystals were then filtered out, washed with diethyl ether, and dried at 35° C. 3.45 g of the difumarate of the title compound having a melting point of 170° C. to 171° C. were obtained.

The compounds of formula I given in the following Table I were also obtained by methods analogous to those described in the foregoing examples.

TABLE I

| Ex. No. | $R^1$ | n | m | Z | $R^2$ | $R^3$ | Salt form, phys. const. m.p. in °C. $[\alpha]_D^{20}$ in ° (c = 1, CH$_3$OH) |
|---|---|---|---|---|---|---|---|
| 20 | (CH$_3$)$_2$CH— | 2 | 2 | O | morph- | dihydronop. | 2 HCl, m.p. = 170–180° |
| 21 | CH$_3$ | 2 | 2 | O | 3,4-di-CH$_3$O-phen-(CH$_2$)$_2$—N—<br>  $\mid$<br>  CH$_3$ | dihydronop. | 2 Fum, m.p. = 155–156° |
| 22 | CH$_3$ | 2 | 2 | O | CH$_3$—CH$_2$—O— | dihydronop. | HCl, m.p. = 72–76° |
| 23 | CH$_3$ | 2 | 2 | O | 3,4-di-CH$_3$O-phen-CH$_2$—N—<br>  $\mid$<br>  CH(CH$_3$)$_2$ | L-menth. | 2 HCl, m.p. = 160–165° |
| 24 | CH$_3$ | 2 | 2 | O | morph- | D-menth. | 2 HCl, m.p. = 200–202 |
| 25 | CH$_3$ | 2 | 2 | O | CH$_3$—CH$_2$—O— | D-menth. | Mal, m.p. = 38–39 |
| 26 | CH$_3$ | 2 | 2 | O | phen-O— | L-menth. | HCl, m.p. = 90–92 |
| 27 | CH$_3$ | 2 | 2 | O | (CH$_3$)$_2$Ch—Ch$_2$—O— | D-menth. | HCl, $[\alpha]_D^{20}$ = +56.4° |
| 28 | CH$_3$ | 2 | 2 | O | (C$_2$H$_5$)$_2$N— | L-menth. | 2 HCl, m.p. = 168–169 |
| 29 | CH$_3$ | 2 | 2 | O | 4-(Phen-CH$_2$) pip- | L-menth. | 3 HCl, m.p. = 215–218 |
| 30 | CH$_3$ | 2 | 2 | O | (CH$_3$)$_2$CH—CH$_2$—O— | L-menth. | Ox, m.p. = 113–115 |
| 31 | CH$_3$ | 2 | 2 | O | phen-CH$_2$—N—<br>  $\mid$<br>  CH$_3$ | L-menth. | 2 HCl m.p. = 170–188 |
| 32 | CH$_3$ | 2 | 2 | O | pyrro- | L-menth. | 2 HCl, m.p. = 225–230 |
| 33 | CH$_3$ | 2 | 2 | O | (CH$_3$)$_2$CH—O | L-menth. | Ox, m.p. = 98–100 |
| 34 | CH$_3$ | 2 | 2 | O | 4-CH$_3$-pip- | L-menth. | 3 HCl, m.p. = 235–239 |
| 35 | CH$_3$ | 2 | 2 | O | phen-CH$_2$—O— | L-menth. | Ox, m.p. = 107–108 |
| 36 | CH$_3$ | 2 | 6 | O | morph- | L-menth. | 2 Ox, m.p. = 113–115 |
| 37 | CH$_3$ | 2 | 2 | O | morph- | fen. | 2 HCl, m.p. = 206–207 |
| 38 | CH$_3$ | 2 | 2 | O | morph- | born | 2 HCl, m.p. = 233–236 |
| 39 | CH$_3$ | 2 | 2 | O | (CH$_3$)$_2$CH—CH$_2$—O— | D-tart, | m.p. = 68–74 |
| 40 | CH$_3$ | 2 | 2 | O | CH$_3$—(CH$_2$)$_4$—O— | L-menth. | HCl, $[\alpha]_D^{20}$ = −53.0° |
| 41 | H | 2 | 2 | O | morph- | L-menth. | 2 HCl, m.p. = 193–199 |
| 42 | CH$_3$ | 3 | 2 | O | morph- | L-menth. | 2 HCl, m.p. = 193–196 |
| 43 | CH$_3$ | 2 | 2 | O | 2-Cl-phen-(CH$_2$)$_2$—NH— | L-menth. | 2 Mal, m.p. = 160–161 |

TABLE I-continued

| Ex. No. | R¹ | n | m | Z | R² | R³ | Salt form, phys. const. m.p. in °C. $[\alpha]_D^{20}$ in ° (c = 1, CH$_3$OH) |
|---|---|---|---|---|---|---|---|
| 44 | CH$_3$ | 2 | 2 | O | 3,4-di-Cl-phen-CH$_2$—NH— | L-menth. | 2 Fum, m.p. = 144–146 |
| 45 | CH$_3$ | 2 | 2 | O | 4,CH$_3$-phen-CH$_2$—NH— | L-menth. | 2 Fum, m.p. = 127–134 |
| 46 | CH$_3$ | 2 | 2 | O | 2-Cl-phen-(CH$_2$)$_2$—N—<br>\|<br>CH$_3$ | L-menth. | 2 Mal, m.p. = 144–145 |
| 47 | CH$_3$ | 2 | 2 | O | 3,4-O—CH$_2$—O-phen-CH$_2$—NH— | L-menth. | 2 Mal, m.p. = 147–149 |
| 48 | CH$_3$ | 2 | 2 | O | phen-CH$_2$—N—<br>\|<br>phen-CH$_2$ | L-menth. | 2 HCl, m.p. = 145–152 |
| 49 | CH$_3$ | 2 | 2 | O | 3-CH$_3$O-phen-(CH$_2$)$_2$—NH— | dihydronop. | 2 Fum, m.p. = 128–130 |
| 50 | CH$_3$ | 2 | 2 | O | phen-(CH$_2$)$_4$—N—<br>\|<br>CH$_3$ | L-menth. | 2 Fum, m.p. = 175–177 |
| 51 | CH$_3$ | 2 | 2 | O | phen-(CH$_2$)$_2$—NH | dihydronop. | 1 Fum m.p. = 151–153° |
| 52 | CH$_3$ | 2 | 2 | O | 3-CF$_3$-phen-CH$_2$—NH | L-menth. | Base $[\alpha]_D^{20}$ = −48.1° |
| 53 | CH$_3$ | 2 | 2 | O | 3,4,5-tri-CH$_3$O-phen-CH$_2$—N—<br>\|<br>2Cl-phen-CH$_2$ | L-menth. | 2 HCl $[\alpha]_D^{20}$ = −30.9° |
| 54 | CH$_3$ | 2 | 2 | O | 3,4-O—CH$_2$O-phen-CH$_2$—N—<br>\|<br>3,4-di-CH$_3$O-phen-CH$_2$ | L-menth. | 2 HCl $[\alpha]_D^{20}$ = −32.1° |
| 55 | CH$_3$ | 2 | 2 | O | 3,4-di-CH$_3$O-phen-CH$_2$—N—<br>\|<br>3,4-di-CH$_3$O-phen-CH$_2$ | L-menth. | 2 Ox m.p. = 92–94° |
| 56 | CH$_3$ | 2 | 2 | O | 2-CH$_3$O-phen-CH$_2$—N—<br>\|<br>2-CH$_3$O-phen-CH$_2$ | L-menth. | 2 Ox m.p. = 67–70° | morph = morpholin-1-yl; phen = phenyl; pip = piperazin-1-yl; pyrro = pyrrolidin-1-yl;
dihydronop. = cis-dihydronopol = (1S,2S,5S)-2-(6,6-dimethylbicyclo[3.3.1]hept-2-yl)ethyl;
L-menth. = L-menthyl = (1R,3R,4S)-1-methyl-4-isopropylcyclohex-3-yl;
D-menth. = D-menthyl = (1S,3S,4R)-1-methyl-4-isopropylcyclohex-3-yl;
fen. = fenchyl = (1S,2R,4R)-1,3,3-trimethylbicyclo[2,2,1]hept-2-yl;
born. = bornyl = (1S,2R,4S)-1,7,7-trimethylbicyclo[2,2,1]hept-2-yl;
HCl = hydrochloride; Fum = fumarate; Mal = maleinate; Ox = oxalate; D-tart = D-tartrate

TABLE II

The following Table II is a listing of starting compounds of Formula X:

| Ex. No. | B | n | m | R² | R³ | Salt form, phys. const. m.p. in °C. $[\alpha]_D^{20}$ in ° (1% in CH$_3$OH) | |
|---|---|---|---|---|---|---|---|
| 101 | bz | 3 | 2 | morph- | L-menth. | 2 Mal. | m.p. = 116–118° |
| 102 | bz | 2 | 2 | (CH$_3$)$_2$CH—CH$_2$—O— | L-menth. | HCl. | $[\alpha]_D^{20}$ = −43.2° |
| 103 | bz | 2 | 2 | (CH$_3$)$_2$CH—O— | L-menth. | HCl. | $[\alpha]_D^{20}$ = −45.4° |
| 104 | bz | 2 | 2 | phen-CH$_2$—N(CH$_3$)— | L-menth. | 2 HCl | m.p. = 152–156° |
| 105 | bz | 3 | 2 | (CH$_3$)$_2$CH—CH$_2$—O— | L-menth. | Mal. | m.p. = 96–97° |

Example I: Tablets containing active compound

Tablets were produced having the following composition per tablet:

| | |
|---|---|
| N-[2-((1R,3R,4S)-1-methyl-4-isopropylcyclohex-3-yloxy)-ethyl]-N-[2-(morpholin-1-yl)ethyl]-N-methylamine dihydrochloride | 20 mg |
| Corn starch | 60 mg |
| Lactose | 135 mg |
| Gelatin (10% solution) | 6 mg |

The active ingredient, the corn starch and the lactose were thickened using the 10% strength gelatin solution to form a paste. The paste was comminuted and the resulting granules were placed on a suitable sheet and dried at 45° C. The dried granules were passed through a comminuting machine and mixed in a mixer with the following adjuvants:

| | |
|---|---|
| Talc | 5 mg |
| Magnesium stearate | 5 mg |
| Corn starch | 9 mg | and then compressed to give 240 mg tablets.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A compound corresponding to the formula I

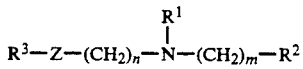

wherein
n represents 2–5,
m represents 2–6,
$R_1$ denotes hydrogen or lower alkyl,
$R_2$ represents an $OR^4$ group in which $R^4$ denotes a lower alkyl, phenyl or phenyl-lower alkyl group which is optionally substituted in the phenyl ring by 1 to 3 substituents selected from the group consisting of lower alkyl, lower alkoxy, halogen and lower alkylenedioxy, or
$R^2$ represents a

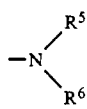

group in which
$R^5$ denotes hydrogen, lower alkyl or a phenyl or phenyl-lower alkyl group which is optionally substituted in the phenyl ring by to 1 to 3 substituents selected from the group consisting of lower alkyl, lower alkoxy, halogen, trifluoromethyl and lower alkylenedioxy, and
$R^6$ denotes hydrogen, lower alkyl or a phenyl or phenyl-lower alkyl group which is optionally substituted in the phenyl ring by 1 to 3 substituents selected from the group consisting of lower alkyl, lower alkoxy, halogen, trifluoromethyl and lower alkylenedioxy, or
$R^5$ and $R^6$, together with the nitrogen atom to which they are bonded, represent a saturated 5- or 6-membered heterocycle, which can optionally contain a second hetero atom from the group of oxygen and N-$R^7$, in which $R^7$ denotes lower alkyl or benzyl,
$R^3$ represents a saturated monocyclic or bicyclic terpene hydrocarbon radical having 10 carbon atoms or a bicyclic hydrocarbon radical having 11 carbon atoms, of the formula b

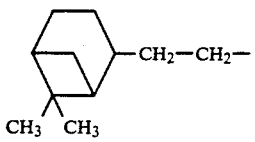

and
Z represents oxygen or, if $R^3$ denotes a radical of the formula b, Z may also represent sulfur,
and physiologically acceptable acid addition salts thereof.

2. A compound according to claim 1, wherein $R^3$ represents a monocyclic or bicyclic hydrocarbon radical having 10 or 11 carbon atoms selected from the group consisting of:

1-methyl-4-isopropylcyclohex-3-yl (=menthyl) of formula a

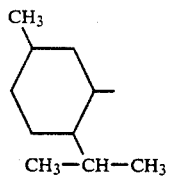

2-(6,6-dimethylbicyclo[3.1.1]hept-2-yl)ethyl (=dihydronopyl) of formula b

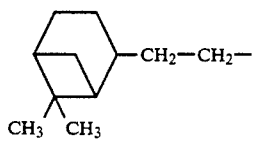

6,6-dimethylbicyclo[3.1.1]hept-2-ylmethyl (=myrtanyl) of formula c

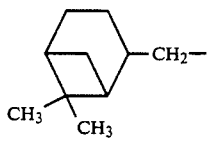

1,3,3-trimethylbicyclo[2.1.1]hept-2-yl (=fenchyl) of formula d

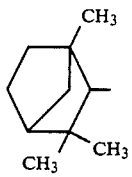

and 1,7,7-trimethylbicyclo[2.2.1]hept-2-yl (=bornyl) of formula e

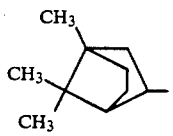

3. A compound according to claim 2, wherein $R^3$ represents a 1-methyl-4-isopropylcyclohex-3-yl group or a 2-(6,6-dimethylbicyclo[3.1.1]hept-2-yl) ethyl group.

4. A compound according to claim 3, wherein $R^3$ represents a 1-methyl-4-isopropylcyclohex-3-yl group which is predominantly in the 1R,3R,4S configuration or the 1S,3S,4R configuration.

5. A compound according to claim wherein $R^3$ represents an

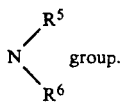 group.

6. A compound according to claim 4, wherein $R^5$ denotes alkyl or a phenyl $C_1$ or $C_2$ alkyl group optionally substituted in the phenyl ring by 1 to 3 substituents selected from the group consisting of lower alkyl, lower alkoxy, halogen, trifluoromethyl and $C_1$ or $C_2$ alkylenedioxy, and $R^6$ denotes a phenyl $C_1$ or $C_2$ alkyl group which is optionally substituted in the phenyl ring by 1 to 3 substituents selected from the group consisting of lower alkyl, lower alkoxy, halogen, trifluoromethyl and $C_1$ or $C_2$ alkylenedioxy, or $R^5$ and $R^6$, together with the nitrogen atom to which they are bonded, represent a 5- or 6-membered saturated heterocycle which optionally contains oxygen as a second hetero atom.

7. A pharmaceutical composition comprising an effective spasmolytic amount of a compound according to claim 1, and at least one conventional pharmaceutical carrier or adjuvant.

* * * * *